United States Patent [19]
Ellenberger et al.

[11] Patent Number: 5,443,978
[45] Date of Patent: Aug. 22, 1995

[54] CHRYSANTHEMYL DIPHOSPHATE SYNTHASE, CORRESPONDING GENES AND USE IN PYRETHRIN SYNTHESIS

[75] Inventors: Suzanne R. Ellenberger, Salem, Utah; Galen D. Peiser, Cupertino, Calif.; Russell N. Bell, Salt Lake City, Utah; Charles E. Hussey, Jr., Salt Lake City, Utah; Donna M. Shattuck-Eidens, Salt Lake City, Utah; Bradley D. Swedlund, Salt Lake City, Utah

[73] Assignee: Agridyne Technologies, Inc., Salt Lake City, Utah

[21] Appl. No.: 82,844

[22] Filed: Jun. 25, 1993

Related U.S. Application Data

[63] Continuation-in-part of Ser. No. 29,480, Mar. 11, 1993, abandoned.

[51] Int. Cl.6 .................. C12N 9/10; C12N 15/54
[52] U.S. Cl. .................. 435/193; 435/240.2; 435/252.3; 435/252.33; 435/320.1; 536/23.2; 536/23.6
[58] Field of Search .................. 536/23.2, 23.6; 435/240.2, 252.3, 252.33, 320.1, 193

[56] References Cited

U.S. PATENT DOCUMENTS
4,525,455  6/1985  Zito et al. .................. 435/135

OTHER PUBLICATIONS
Banthorpe et al. (1977) *Phytochemistry* 16:85–92.
Casida (1973) "*Pyrethrum, The Natural Insecticide,*" J.E. Casida, ed., Academic Press, N.Y., pp. 101–120.
Manitto (1981), "*Biosynthesis of Natural Products,*" Wiley and Sons, N.Y., pp. 94–97.
Romanet et al. (1974) *J. Am. Chem. Soc.* 96:3701–3702.
Brasher et al. (1954) *J. Am. Chem. Soc.* 76:114–115.
Davisson et al. (1986) *J. Org. Chem.* 51:4768–4779.
Dixit et al. (1981) *J. Org. Chem.* 46:1967–1970.
Carter (1989) *Pesticide Science* 27:361–374.
Elliott (1989) *Pesticide Science* 27:337–351.
Bushell (1989) "Recent Advances in the Chemistry of Insect Control II," (L. Crombie, ed.) *Royal Society of Chemistry*, Special Publication No. 79, pp. 125–141.
Pongor, S. 1987. Methods in Enzymology, 154:450–473.
Creighton, T. E. Proteins: Structure and Molecular Principels. W. H. Freeman and Company, N.Y. 1983. pp. 93–98.

*Primary Examiner*—Keith C. Furman
*Attorney, Agent, or Firm*—Greenlee and Winner

[57] ABSTRACT

This invention provides a purified chrysanthemyl diphosphate synthase (CDS), a method for the purification of CDS from *Chrysanthemum cinerariaefolium*, and an amino acid sequence of the isolated CDS. Also provided is a cDNA encoding the CDS, a nucleotide sequence of the CDS gene, and a derived amino acid sequence of the encoded CDS protein. The CDS gene is useful in the enzymatic production of the natural stereospecific configuration of chrysanthemyl derivatives which are useful for the synthesis of pyrethrins, pyrethroids, derivatives thereof, as well as other classes of metabolites.

35 Claims, 8 Drawing Sheets

Biosynthesis of Chrysanthemic Acid

Pyrethrin Esters

| | | |
|---|---|---|
| Pyrethrin I : | R=CH$_3$ | R'=CH$_2$CH=CHCH=CH$_2$ |
| Pyrethein II: | R=COOCH$_3$ | R'=CH$_2$CH=CHCH=CH$_2$ |
| Cinerin I : | R=CH$_3$ | R'=CH$_2$CH=CHCH$_3$ |
| Cinerin II : | R=COOCH$_3$ | R'=CH$_2$CH=CHCH$_3$ |
| Jasmolin I : | R=CH$_3$ | R'=CH$_2$CH=CHCH$_2$CH$_3$ |
| Jasmolin II : | R=COOCH$_3$ | R'=CH$_2$CH=CHCH$_2$CH$_3$ |

Biosynthesis of Chrysanthemic Acid

Combined Chemical and Biological Preparation of Pyrethrins

Figure 4A

Nucleotide Sequence of the CDS Gene Fragment
(SEQ ID NO:10)

| | |
|---|---:|
| TCGGCACGAG ATTCGGCACG AGAAATGGCT TGCTCTAGTA GGTACTAGTT | 50 |
| ACTCTTATTG CTATAAACAT ATTGCTTAAT TCATGATGTC CTAGCGAGCA | 100 |
| ATTGTGACAG CATCCGAATG ATGATATATA TGGGCGATCT ACATATAAAA | 150 |
| TACTCCTAGA TCGATGTGCA TTTAGTAGAA ATATACTTAT TTAAAGATAT | 200 |
| AAAAAATGTC CGCACTTGTT ATGATTCCAT GATATATA | 238 |

| | |
|---|---:|
| ATG TCT TGG TGT CTC TTA TGC AGT CTT TCT TCC AAA TGG GCT<br>Met Ser Trp Cys Leu Leu Cys Ser Leu Ser Ser Lys Trp Ala<br>1                      5                       10 | 280 |
| TCT TGG GGT GCC TCT TCT CGT CCG CAC CCA TCA GTT CAA CCT<br>Ser Trp Gly Ala Ser Ser Arg Pro His Pro Ser Val Gln Pro<br>15                   20                     25 | 322 |
| TTT GTG ACT CGA AAG AAT GTG GTA CGG TAT CAT AAA CCA ACC<br>Phe Val Thr Arg Lys Asn Val Val Arg Tyr His Lys Pro Thr<br>     30                     35                   40 | 364 |
| TCT GAG TTA AGC TAT TCT CCT CTC ACT ACG ACA TTG AGC AGC<br>Ser Glu Leu Ser Tyr Ser Pro Leu Thr Thr Thr Leu Ser Ser<br>         45                    50                 55 | 406 |
| AAT CTA GAC TCA CAA TTC ATG CAA GTT TAT GAG ACT TTG AAA<br>Asn Leu Asp Ser Gln Phe Met Gln Val Tyr Glu Thr Leu Lys<br>              60                   65               70 | 448 |
| TCT GAG CTA ATT CAT GAC CCG TCA TTT GAG TTT GAT GAC GAT<br>Ser Glu Leu Ile His Asp Pro Ser Phe Glu Phe Asp Asp Asp<br>                  75                       80 | 490 |
| TCT CGT CAG TGG GTG GAG CGG ATG ATT GAC TAC AAT GTA CCT<br>Ser Arg Gln Trp Val Glu Arg Met Ile Asp Tyr Asn Val Pro<br>85                      90                     95 | 532 |
| GGA GGA AAG ATG GTC CGA GGC TAT TCT GTT GTT GAC AGC TAC<br>Gly Gly Lys Met Val Arg Gly Tyr Ser Val Val Asp Ser Tyr<br>     100                  105               110 | 574 |
| CAA TTG CTT AAA GGA GAA GAA TTG ACG GAA GAT GAA GCT TTT<br>Gln Leu Leu Lys Gly Glu Glu Leu Thr Glu Asp Glu Ala Phe<br>         115                  120              125 | 616 |

Figure 4B

| | |
|---|---|
| CTC GCG TGT GCT CTT GGT TGG TGC ACT GAA TGG CTT CAA GCC<br>Leu Ala Cys Ala Leu Gly Trp Cys Thr Glu Trp Leu Gln Ala<br>     130                     135                     140 | 658 |
| TTT ATA CTT GTC CTT GAT GAC ATA ATG GAT GGC TCG CAC ACA<br>Phe Ile Leu Val Leu Asp Asp Ile Met Asp Gly Ser His Thr<br>              145                     150 | 700 |
| CGT AGA GGT CAA CCC TGT TGG TTT AGA CTA CCC GAG GTT GGA<br>Arg Arg Gly Gln Pro Cys Trp Phe Arg Leu Pro Glu Val Gly<br>155                     160                     165 | 742 |
| GTA GTT GCT ATA AAT GAT GGT GTT CTT CTT CGC AAC CAT GTG<br>Val Val Ala Ile Asn Asp Gly Val Leu Leu Arg Asn His Val<br>     170                     175                     180 | 784 |
| CAT AGA ATA CTG AAG AAA TAT TTC CAA GGA AAG CCT TAT TAC<br>His Arg Ile Leu Lys Lys Tyr Phe Gln Gly Lys Pro Tyr Tyr<br>              185                     190                     195 | 826 |
| GTG CAT CTT CTG GAC CTC TTC AAT GAG ACC GAA TTT CAA ACA<br>Val His Leu Leu Asp Leu Phe Asn Glu Thr Glu Phe Gln Thr<br>              200                     205                     210 | 868 |
| ATC TCT GGA CAA ATG ATT GAT ACA ATA TGT AGA CTA GCT GGA<br>Ile Ser Gly Gln Met Ile Asp Thr Ile Cys Arg Leu Ala Gly<br>              215                     220 | 910 |
| CAA AAA GAT CTT TCA AAG TAT ACT ATG ACT CTT AAC CGT CGG<br>Gln Lys Asp Leu Ser Lys Tyr Thr Met Thr Leu Asn Arg Arg<br>225                     230                     235 | 952 |
| ATT GTT CAG TAC AAA GGT TCT TAC TAC TCA TGT TAC CTT CCA<br>Ile Val Gln Tyr Lys Gly Ser Tyr Tyr Ser Cys Tyr Leu Pro<br>     240                     245                     250 | 994 |
| ATT GCG TGT GCA CTC CTT ATG TTT GGA GAG AAT CTG GAA GAT<br>Ile Ala Cys Ala Leu Leu Met Phe Gly Glu Asn Leu Glu Asp<br>              255                     260                     265 | 1036 |
| CAT GTT CAA GTG AAA GAC ATC CTT GTA GAA TTG GGT ATG TAT<br>His Val Gln Val Lys Asp Ile Leu Val Glu Leu Gly Met Tyr<br>              270                     275                     280 | 1078 |
| TAT CAA ATT CAG AAT GAT TAT CTC GAC ACT TTT GGT GAT CCT<br>Tyr Gln Ile Gln Asn Asp Tyr Leu Asp Thr Phe Gly Asp Pro<br>              285                     290 | 1120 |
| GAT GTT TTT GGA AAG ACG GGA ACA GAT ATT GAA GAA TGC AAG<br>Asp Val Phe Gly Lys Thr Gly Thr Asp Ile Glu Glu Cys Lys<br>295                     300                     305 | 1162 |

Figure 4C

| | |
|---|---|
| TGT TCA TGG TTG ATT GCA AAA GCA CTG GAA CTT GCC AAC GAG<br>Cys Ser Trp Leu Ile Ala Lys Ala Leu Glu Leu Ala Asn Glu<br>         310                   315                   320 | 1204 |
| GAA CAA AAG AAA ATT TTA AGC GAA AAC TAT GGG ATA AAC GAT<br>Glu Gln Lys Lys Ile Leu Ser Glu Asn Tyr Gly Ile Asn Asp<br>         325                   330                   335 | 1246 |
| CCA TCA AAG GTA GCA AAA GTG AAG GAA TTA TAC CAT GCT CTT<br>Pro Ser Lys Val Ala Lys Val Lys Glu Leu Tyr His Ala Leu<br>         340                   345                   350 | 1288 |
| GAT CTA AAG GGT GCG TAT GAA GAT TAT GAG ACA AAT CTT TAT<br>Asp Leu Lys Gly Ala Tyr Glu Asp Tyr Glu Thr Asn Leu Tyr<br>                  355                        360 | 1330 |
| GAG ACG TCA ATG ACA TCA ATT AAA GCT CAT CCA AAC ATT GCA<br>Glu Thr Ser Met Thr Ser Ile Lys Ala His Pro Asn Ile Ala<br>365                        370                   375 | 1372 |
| GTG CAA GCG GTG TTG AAA TCT TGT CTG GAA AAG ATG TAT AAG<br>Val Gln Ala Val Leu Lys Ser Cys Leu Glu Lys Met Tyr Lys<br>         380                   385                   390 | 1414 |
| GGA CAT AAG TAACTTAGCT GGATTGATTC<br>Gly His Lys<br>         395 | 1443 |
| TTAGTTTCTT TAGAGGTCAT ATAGTGTATT TATCGGCCAT TGTATGCTGG | 1493 |
| ATATTCATAT TCATGATATC ATGAAACATG GTAATAGAAT AATAATAAGG | 1543 |
| ATGTCAATAA AAAGAACATG AAGTCATTGG TTATTATTAT CAAATTTTCT | 1593 |
| CTATTACACA CTATCAAAAA AAAAAAAAAA AA | 1625 |

FIG. 5
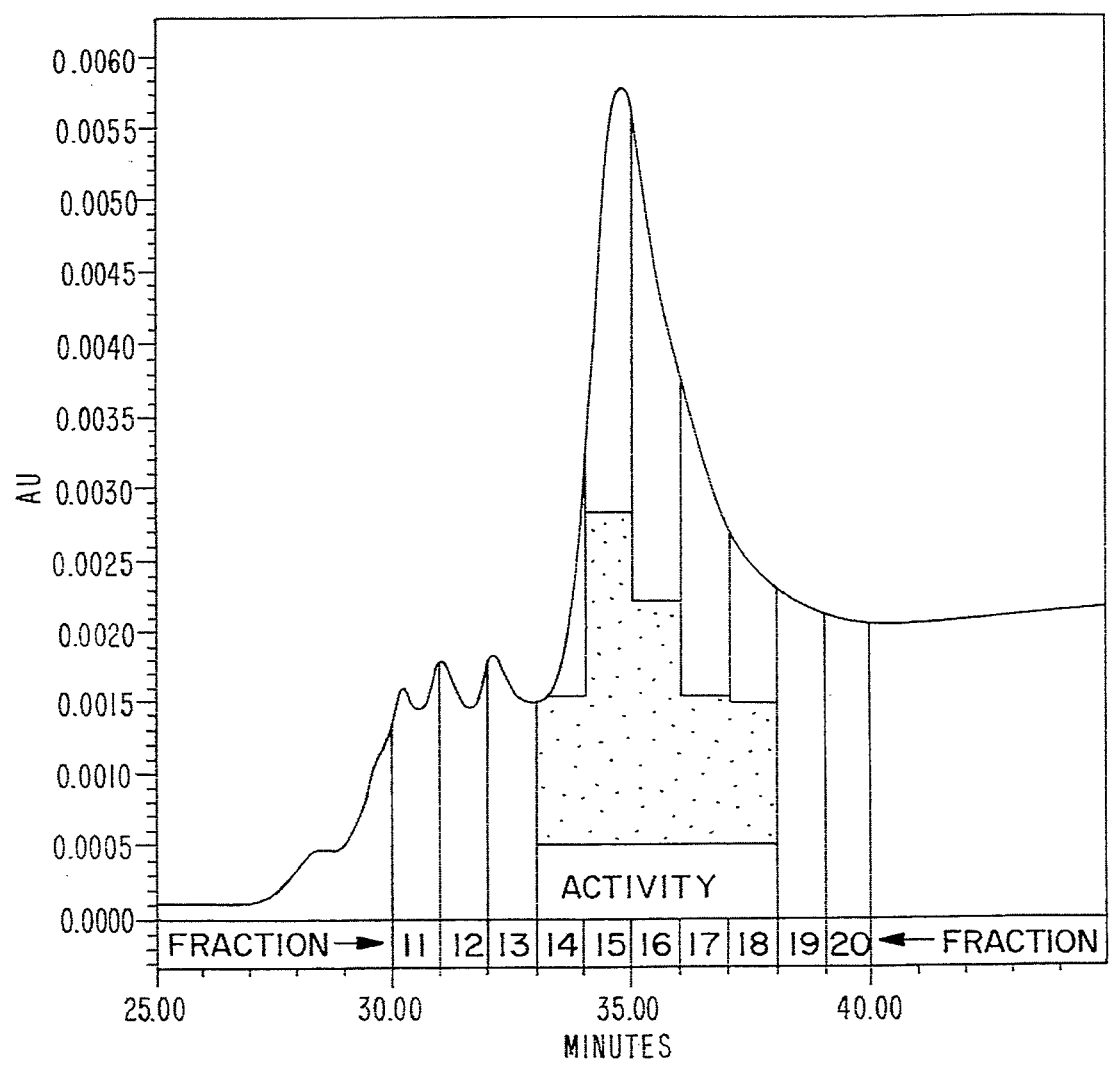
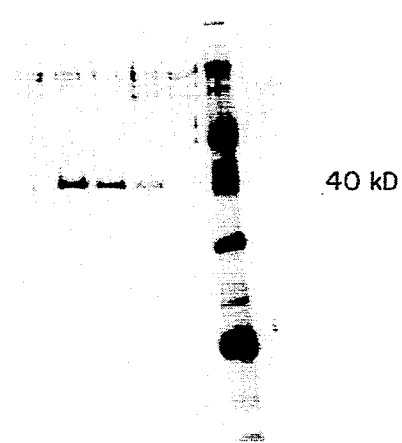
FRACTIONS  14  15  16  17  18  MWM

Synthesis of Dimethylallyl Pyrophosphate (DMAPP)

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: misc feature
        ( B ) LOCATION: 1..20
        ( D ) OTHER INFORMATION: /note=""""N-terminal amino acid
            sequence of CDS after phenyl sepharose
            chromatography.""""

( x i ) SEQUENCE DESCRIPTION: SEQ ID NO:1:

```
Thr  Thr  Thr  Leu  Ser  Ser  Asn  Leu  Asp  Ser  Gln  Phe  Met  Gln  Val  Tyr
1                  5                        10                       15

Glu  Thr  Leu  Lys
                20
```

( 2 ) INFORMATION FOR SEQ ID NO:2:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1..14
        ( D ) OTHER INFORMATION: /label=Xaa
            / note="Xaa equals residues which could not be
            identified with certainty."

( x i ) SEQUENCE DESCRIPTION: SEQ ID NO:2:

```
Thr  Thr  Thr  Leu  Ser  Ser  Asn  Leu  Asp  Xaa  Gln  Phe  Xaa  Gln
1                  5                        10
```

( 2 ) INFORMATION FOR SEQ ID NO:3:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

```
Ile  Leu  Ser  Glu  Asn  Tyr  Gly  Ile  Asn  Asp  Pro  Ser  Lys
1                  5                        10
```

( 2 ) INFORMATION FOR SEQ ID NO:4:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

```
Ala His Pro Asn Ile Ala Val Gln Ala Val Leu Lys
 1               5                   10
```

( 2 ) INFORMATION FOR SEQ ID NO:5:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1..7
        ( D ) OTHER INFORMATION: /label=Xaa
            / note="Xaa equals residues which could not be identified with certainty."

( x i ) SEQUENCE DESCRIPTION: SEQ ID NO:5:

```
Xaa Leu Tyr His Ala Leu Asp
 1               5
```

( 2 ) INFORMATION FOR SEQ ID NO:6:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

```
Val Lys Gly Leu Tyr His Ala Leu Asp Leu Lys
 1               5                   10
```

( 2 ) INFORMATION FOR SEQ ID NO:7:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1..15
        ( D ) OTHER INFORMATION: /label=Xaa
            / note="Xaa equals residues which could not be identified with certainty."

( x i ) SEQUENCE DESCRIPTION: SEQ ID NO:7:

```
Xaa Ala Tyr Glu Asp Tyr Glu Thr Asn Leu Tyr Glu Thr Ser Met Thr
 1               5                   10                  15
Ser Ile
```

( 2 ) INFORMATION FOR SEQ ID NO:8:

(i) SEQUENCE CHARACTERISTICS:
    (A) LENGTH: 11 amino acids
    (B) TYPE: amino acid
    (C) STRANDEDNESS: single
    (D) TOPOLOGY: linear (ii) MOLECULE TYPE: peptide (ix) FEATURE:
    (A) NAME/KEY: Modified-site
    (B) LOCATION: 1..11
    (D) OTHER INFORMATION: /label=Xaa
        / note="Xaa equals residues which could not be
        identified with certainty."

(xi) SEQUENCE DESCRIPTION: SEQ ID NO:8:

Xaa  Ala  Tyr  Glu  Asp  Tyr  Glu  Ser  Asn  Glu  Tyr
 1              5                        10

(2) INFORMATION FOR SEQ ID NO:9:

(i) SEQUENCE CHARACTERISTICS:
    (A) LENGTH: 23 base pairs
    (B) TYPE: nucleic acid
    (C) STRANDEDNESS: single
    (D) TOPOLOGY: linear (ii) MOLECULE TYPE: DNA (genomic)

(ix) FEATURE:
    (A) NAME/KEY: modifiedbase
    (B) LOCATION: 1..23
    (D) OTHER INFORMATION: /modbase=i
        / note="AT POSITION 15 N =INOSINE"

(xi) SEQUENCE DESCRIPTION: SEQ ID NO:9:

CARTTYATGC ARGTNTAYGA RAC    23

(2) INFORMATION FOR SEQ ID NO:10:

(i) SEQUENCE CHARACTERISTICS:
    (A) LENGTH: 1625 base pairs
    (B) TYPE: nucleic acid
    (C) STRANDEDNESS: single
    (D) TOPOLOGY: linear (ii) MOLECULE TYPE: cDNA (ix) FEATURE:
    (A) NAME/KEY: miscfeature
    (B) LOCATION: 239..241
    (D) OTHER INFORMATION: /note="first met codon"

(ix) FEATURE:
    (A) NAME/KEY: miscfeature
    (B) LOCATION: 389..448
    (D) OTHER INFORMATION: /note="corresponds to the N-
        terminal amino acid sequence of the CDS protein
        of
        Table 2."

(ix) FEATURE:
    (A) NAME/KEY: miscfeature
    (B) LOCATION: 1217..1255
    (D) OTHER INFORMATION: /note="corresponds to the CDS
        tryptic peptide of peak 2 (Table 4)."

(ix) FEATURE:
    (A) NAME/KEY: miscfeature
    (B) LOCATION: 1265..1297
    (D) OTHER INFORMATION: /note="corresponds to the CDS
        tryptic peptide of peak 5 (Table 7)."

(ix) FEATURE:
    (A) NAME/KEY: miscfeature
    (B) LOCATION: 1301..1351
    (D) OTHER INFORMATION: /note="corresponds to the CDS -continued tryptic peptide of peak 6 (Table 8)."

( i x ) FEATURE:
  ( A ) NAME/KEY: miscfeature
  ( B ) LOCATION: 1355..1390
  ( D ) OTHER INFORMATION: /note="corresponds to the CDS
    tryptic peptide of peak 4 (Table 5)."

( i x ) FEATURE:
  ( A ) NAME/KEY: CDS
  ( B ) LOCATION: 239..1423

( x i ) SEQUENCE DESCRIPTION: SEQ ID NO:10:

```
TCGGCACGAG ATTCGGCACG AGAAATGGCT TGCTCTAGTA GGTACTAGTT ACTCTTATTG   60

CTATAAACAT ATTGCTTAAT TCATGATGTC CTAGCGAGCA ATTGTGACAG CATCCGAATG  120

ATGATATATA TGGGCGATCT ACATATAAAA TACTCCTAGA TCGATGTGCA TTTAGTAGAA  180

ATATACTTAT TTAAAGATAT AAAAAATGTC CGCACTTGTT ATGATTCCAT GATATATA    238

ATG TCT TGG TGT CTC TTA TGC AGT CTT TCT TCC AAA TGG GCT TCT TGG   286
Met Ser Trp Cys Leu Leu Cys Ser Leu Ser Ser Lys Trp Ala Ser Trp
 1           5                  10                 15

GGT GCC TCT TCT CGT CCG CAC CCA TCA GTT CAA CCT TTT GTG ACT CGA   334
Gly Ala Ser Ser Arg Pro His Pro Ser Val Gln Pro Phe Val Thr Arg
             20                 25                 30

AAG AAT GTG GTA CGG TAT CAT AAA CCA ACC TCT GAG TTA AGC TAT TCT   382
Lys Asn Val Val Arg Tyr His Lys Pro Thr Ser Glu Leu Ser Tyr Ser
         35                 40                 45

CCT CTC ACT ACG ACA TTG AGC AGC AAT CTA GAC TCA CAA TTC ATG CAA   430
Pro Leu Thr Thr Thr Leu Ser Ser Asn Leu Asp Ser Gln Phe Met Gln
     50                 55                 60

GTT TAT GAG ACT TTG AAA TCT GAG CTA ATT CAT GAC CCG TCA TTT GAG   478
Val Tyr Glu Thr Leu Lys Ser Glu Leu Ile His Asp Pro Ser Phe Glu
 65                 70                 75                 80

TTT GAT GAC GAT TCT CGT CAG TGG GTG GAG CGG ATG ATT GAC TAC AAT   526
Phe Asp Asp Asp Ser Arg Gln Trp Val Glu Arg Met Ile Asp Tyr Asn
                 85                 90                 95

GTA CCT GGA GGA AAG ATG GTC CGA GGC TAT TCT GTT GTT GAC AGC TAC   574
Val Pro Gly Gly Lys Met Val Arg Gly Tyr Ser Val Val Asp Ser Tyr
            100                105                110

CAA TTG CTT AAA GGA GAA GAA TTG ACG GAA GAT GAA GCT TTT CTC GCG   622
Gln Leu Leu Lys Gly Glu Glu Leu Thr Glu Asp Glu Ala Phe Leu Ala
        115                120                125

TGT GCT CTT GGT TGG TGC ACT GAA TGG CTT CAA GCC TTT ATA CTT GTC   670
Cys Ala Leu Gly Trp Cys Thr Glu Trp Leu Gln Ala Phe Ile Leu Val
    130                135                140

CTT GAT GAC ATA ATG GAT GGC TCG CAC ACA CGT AGA GGT CAA CCC TGT   718
Leu Asp Asp Ile Met Asp Gly Ser His Thr Arg Arg Gly Gln Pro Cys
145                150                155                160

TGG TTT AGA CTA CCC GAG GTT GGA GTA GTT GCT ATA AAT GAT GGT GTT   766
Trp Phe Arg Leu Pro Glu Val Gly Val Val Ala Ile Asn Asp Gly Val
                165                170                175

CTT CTT CGC AAC CAT GTG CAT AGA ATA CTG AAG AAA TAT TTC CAA GGA   814
Leu Leu Arg Asn His Val His Arg Ile Leu Lys Lys Tyr Phe Gln Gly
            180                185                190

AAG CCT TAT TAC GTG CAT CTT CTG GAC CTC TTC AAT GAG ACC GAA TTT   862
Lys Pro Tyr Tyr Val His Leu Leu Asp Leu Phe Asn Glu Thr Glu Phe
        195                200                205

CAA ACA ATC TCT GGA CAA ATG ATT GAT ACA ATA TGT AGA CTA GCT GGA   910
Gln Thr Ile Ser Gly Gln Met Ile Asp Thr Ile Cys Arg Leu Ala Gly
    210                215                220

CAA AAA GAT CTT TCA AAG TAT ACT ATG ACT CTT AAC CGT CGG ATT GTT   958
Gln Lys Asp Leu Ser Lys Tyr Thr Met Thr Leu Asn Arg Arg Ile Val
225                230                235                240
```

```
CAG TAC AAA GGT TCT TAC TAC TCA TGT TAC CTT CCA ATT GCG TGT GCA    1006
Gln Tyr Lys Gly Ser Tyr Tyr Ser Cys Tyr Leu Pro Ile Ala Cys Ala
                245                 250                 255

CTC CTT ATG TTT GGA GAG AAT CTG GAA GAT CAT GTT CAA GTG AAA GAC    1054
Leu Leu Met Phe Gly Glu Asn Leu Glu Asp His Val Gln Val Lys Asp
                260                 265                 270

ATC CTT GTA GAA TTG GGT ATG TAT TAT CAA ATT CAG AAT GAT TAT CTC    1102
Ile Leu Val Glu Leu Gly Met Tyr Tyr Gln Ile Gln Asn Asp Tyr Leu
                275                 280                 285

GAC ACT TTT GGT GAT CCT GAT GTT TTT GGA AAG ACG GGA ACA GAT ATT    1150
Asp Thr Phe Gly Asp Pro Asp Val Phe Gly Lys Thr Gly Thr Asp Ile
                290                 295                 300

GAA GAA TGC AAG TGT TCA TGG TTG ATT GCA AAA GCA CTG GAA CTT GCC    1198
Glu Glu Cys Lys Cys Ser Trp Leu Ile Ala Lys Ala Leu Glu Leu Ala
305                 310                 315                 320

AAC GAG GAA CAA AAG AAA ATT TTA AGC GAA AAC TAT GGG ATA AAC GAT    1246
Asn Glu Glu Gln Lys Lys Ile Leu Ser Glu Asn Tyr Gly Ile Asn Asp
                325                 330                 335

CCA TCA AAG GTA GCA AAA GTG AAG GAA TTA TAC CAT GCT CTT GAT CTA    1294
Pro Ser Lys Val Ala Lys Val Lys Glu Leu Tyr His Ala Leu Asp Leu
                340                 345                 350

AAG GGT GCG TAT GAA GAT TAT GAG ACA AAT CTT TAT GAG ACG TCA ATG    1342
Lys Gly Ala Tyr Glu Asp Tyr Glu Thr Asn Leu Tyr Glu Thr Ser Met
                355                 360                 365

ACA TCA ATT AAA GCT CAT CCA AAC ATT GCA GTG CAA GCG GTG TTG AAA    1390
Thr Ser Ile Lys Ala His Pro Asn Ile Ala Val Gln Ala Val Leu Lys
        370                 375                 380

TCT TGT CTG GAA AAG ATG TAT AAG GGA CAT AAG TAACTTAGCT GGATTGATTC  1443
Ser Cys Leu Glu Lys Met Tyr Lys Gly His Lys
385                 390                 395

TTAGTTTCTT TAGAGGTCAT ATAGTGTATT TATCGGCCAT TGTATGCTGG ATATTCATAT  1503

TCATGATATC ATGAAACATG GTAATAGAAT AATAATAAGG ATGTCAATAA AAAGAACATG  1563

AAGTCATTGG TTATTATTAT CAAATTTTCT CTATTACACA CTATCAAAAA AAAAAAAAAA  1623

AA                                                                 1625
```

CHRYSANTHEMYL DIPHOSPHATE SYNTHASE, CORRESPONDING GENES AND USE IN PYRETHRIN SYNTHESIS

RELATEDNESS OF THE INVENTION

The subject application is a continuation-in-part of U.S. application Ser. No. 08/029,480, now abandoned, filed on Mar. 11, 1993, which is incorporated herein in the entirety by reference.

FIELD OF INVENTION

This invention relates to a gene encoding chrysanthemyl diphosphate synthase (CDS) and its use in pyrethrin production. In particular, chrysanthemyl diphosphate synthase was purified from *Chrysanthemum cinerariaefolium*, its partial amino acid sequences at the N-terminal region and from internal fragments obtained from tryptic digests was determined, and a gene encoding the sequence was identified and sequenced. The CDS gene is useful for the enzymatic production of the natural stereospecific configuration of chrysanthemic acid which can be used critically in an economically feasible synthesis of pyrethrins.

BACKGROUND OF THE INVENTION

Insecticidal properties of pyrethrum have been known for many years, dating back to folk entomology and has been safely used, handled, and dispersed in the home and around pets, people, domestic animals and food plants. Pyrethrum is the name applied to compounds produced by *Chrysanthemum cinerariaefolium* and *Chrysanthemum coccineum*, plants which produce and store within the oil glands of the flowers six closely related esters known as pyrethrins (see FIG. 1), the most potent of which are pyrethrins I and II. When extracted, these pyrethrin compounds are nonpersistent insecticides with relatively low toxicity to mammals. The term pyrethrum is also used to refer to the commercial extract from pyrethrin flowers which contains the pyrethrin esters.

Industrially, pyrethrum extracts are obtained by extraction of dried pyrethrum flowers with hexane followed by dewaxing and decolorization to yield a mixture containing approximately 20% pyrethrins and 80% inert plant materials or solvents. This technical extract is registered with the Environmental Protection Agency and is a standard item of commerce used for formulating numerous end products. Flower production is centered in Kenya and surrounding countries, with some production being attempted in Tasmania and New Guinea. While pyrethrum flowers are not grown commercially in the United States, some of the Compositae (daisies, marigolds, etc.) in U.S. gardens probably produce these compounds. There has been an effort to cultivate *C. cinerariaefolium* in Oregon and Arizona but this is not yet a viable commercial source.

Recent trends toward the use of pesticides with greater environmental safety are causing an increase in pyrethrum demand, but the supply has remained relatively constant. Market demand exceeds supply by more than four times, thus generating a need to find an inexpensive method for chemically producing pyrethrins.

Synthetic pyrethroids have been developed which are more efficacious and longer lasting than pyrethrin, but these improvements are accompanied by increased toxicity and persistence of toxic residues. Compared with synthetic pyrethroids, pyrethrin has the favorable characteristic of being highly efficacious on a broad spectrum of insects while still being environmentally safe. To increase the supply of pyrethrins, the extraction/isolation methods currently used can be improved in such factors as (1) enhanced yield (2) decreased contamination by inert plant material and (3) delivery of a specific ratio of the six pyrethrins. Alternatively, pyrethrins can be chemically synthesized. To obtain optimal activity from a synthetic pyrethrin, the molecule(s) must have the correct three-dimensional spatial configuration (stereochemistry) because the incorrect stereoisomers are significantly less active as insecticides. Although stereospecific synthesis of pyrethrins utilizing synthetic organic methods is possible, the cost is prohibitive which causes continued reliance on extracts from flowers. Reactions contemplated in the synthesis of pyrethrins are schematically presented in FIGS. 2 and 3.

Pyrethrin molecules are composed of two distinct parts, a substituted cyclopropyl carboxylic acid and an unsaturated keto-alcohol entity. The cyclopropyl carboxylic acid part of the molecule, chrysanthemic or pyrethric acid, possesses complex stereochemistry. Chrysanthemic acid contains two asymmetric centers with the possibility of yielding four isomers. Pyrethric acid contains the same asymmetric centers and additionally has the possibility of cis-trans isomerism in the vinyl side chain to yield eight possible isomers.

The absolute configuration of the cyclopropane part of the pyrethrate esters, (+)-trans-chrysanthemic acid and (+)-trans-trans-pyrethric acid, have been determined chemically [Crombie, L. (1954) J. Chem. Soc., London, 470], and spectroscopically, [Begley, M. J. et al. (1972) J. Chem. Soc., Chem. Commun., 1276]. The naturally occurring configurations are insecticidally more active than the racemic mixture or any of the synthetic isomers. Because of the complex stereochemistry and thus difficulty in preparing chrysanthemic acid stereo- and enantiospecifically, a biological approach to this material is attractive as an economically feasible alternative.

Rethrolones, which is the collective name applied to the keto-alcohol components of the insecticidal pyrethrin esters, are a group of closely related cyclopentenones. Some studies have indicated that the rethrolone portion of the molecule is synthesized through a pathway different than chrysanthemic acid since label from $^{14}C$-acetate is found on the rethrolone portion of the molecule, but not from $^{14}C$-mevalonate. Although specific information is not available, it has been suggested that fatty acids, such as linoleic acid, are biosynthetic intermediates of the rethrolone portion of pyrethrin molecules, [Vick, B. A. et al. (1984) Plant Physiol. 75:458; Vick, B. A. et al (1987) Plant Physiol. 85:1073; Crombie, L. et al. (1985) Perkin Trans. I, p. 1393; Hildebrand, D. F. (1989) Physiol. Plant 76:249].

The rethrolone keto-alcohols have one asymmetric carbon at the 4-position and a double bond(s) in the side chain which is capable of cis-trans isomerism in the 2-position. It is therefore possible to have up to four stereoisomers for each keto-alcohol. It has been shown that only the (+) form occurs in the natural esters and that the natural configurations are insecticidally more active, [Elliot, M. et al. (1971) J. Chem. Soc., p. 2548; Katsuda, Y. et al. (1958) Bull. Agr. Chem. Soc. Japan 22:427].

It has been established that biosynthesis of the cyclopropane moiety of pyrethrin molecules, chrysanthemic or pyrethric acid, stems from mevalonic acid as the starting material. [Pattenden, G. et al. (1973) Tetrahedron Lett. 36:3473; Abou-Donia, S. A. et al. (1973) Tetrahedron Lett. 36:3477; Crombie, L. (1980) Pestic Sci. 11:102; Pattenden, G. (1970) Pyrethrum Post 10(4):2; Levy, L. W. et al. (1960) Pyrethrum Post 5(4):3].

Reactions 1 to 4 in FIG. 2 occur in all organisms which convert mevalonic acid to dimethylallyl pyrophosphate (DMAPP), the proposed 5-carbon precursor to chrysanthemyl diphosphate). The enzymes responsible for these reactions have been purified. Isopentenyl pyrophosphate (also called isopentenyl diphosphate) and DMAPP are the precursors to many metabolites including sterols, pigments and certain vitamins. The enzyme responsible for the interconversion of isopentenyl diphosphate and DMAPP (reaction 4) is isopentenyl pyrophosphate isomerase (EC 5.3.3.2) which has been purified from various animals and bacteria, [Satterwhite, D. M. (1985) Methods Enzymol. 110:92], and plants such as Capsicum, Dogbo, O. et al. (1987) Biochim. Biophys. Acta 920:140; daffodils, Lutzow, M. et al. (1988) Biochim. Biophys. Acta 959:118]; and tomato, Spurgeon, S. L. et al. (1984) Arch. Biochem. Biophys. 230(2):446–454].

Chrysanthemic acid has been reported to be synthesized in certain members of the Compositae family, including species of Chrysanthemum, Tagetes, Artemisia and Santolina, [Zito, S. W. et al. (1985) U.S. Pat. No. 4,525,455, Banthorpe et al. (1977) Phytochemistry 16:85]. It was suggested [Casida, J. E. (1973) "Pyrethrum, The Natural Insecticide," Casida, ed., Academic Press, New York, pp. 101–120; Manitto, P. (1981) "Biosynthesis of Natural Products," Wiley & Sons, New York, pp . 94–95], that two molecules of DMAPP condense to produce chrysanthemyl diphosphate (also called chrysanthemyl pyrophosphate; reaction 5 in FIG. 2). Although the exact mechanism of this novel proposed combination of C-5 units is unknown, it was suggested to be a "non-head-to-tail" condensation and thus was unlike the reactions which lead to the synthesis of most other isoprenoids. There are no reports on the purification of the enzyme responsible for the formation of chrysanthemyl diphosphate, so it has not been established that DMAPP is the immediate precursor for this intermediate. Zito and Staba (U.S. Pat. No. 4,525,455) have demonstrated that both $^{14}$C-mevalonic acid and $^{14}$C-isopentenyl diphosphate produce $^{14}$C-chrysanthemyl diphosphate using a cell-free homogenate from *C. cinerariaefolium*. Using crude enzyme homogenates from *Artemisia annua* and *Santolina chamaecyparissus*, Banthorpe, D. V. (1977) Phytochemistry 16:85 demonstrated that $^{14}$C-DMAPP and $^{14}$C-dimethylvinylcarbinol were converted to chrysanthemyl diphosphate. The work by Zito and Stabe, supra indicates that the enzymes forming chrysanthemyl diphosphate and the other enzymes involved in pyrethrin formation are cytosolic, since essentially all activity was found in the 100,000 X g supernatant and little to no activity was observed in the proplastid and mitochondrial fractions.

The enzyme responsible for the putative condensation reaction to form chrysanthemyl diphosphate from DMAPP is designated chrysanthemyl diphosphate synthase (CDS) and is a prenyltransferase. Prenyltransferases (EC 2.5.1.x) catalyze the transfer of an isoprenoid diphosphate to another isoprenoid diphosphate or to a nonisoprenoid acceptor. That only one enzyme could be involved in the conversion of DMAPP to chrysanthemyl diphosphate is analogous to the enzymatic function of a different prenyltransferase which, even when purified to homogeneity, exhibits two catalytic activities, (Dogbo, O. et al. (1988) Proc. Natl. Acad. Sci. USA 85:7054). This prenyltransferase protein, designated phytoene synthase, couples two molecules of geranylgeranyl diphosphate to yield prephytoene diphosphate and then converts prephytoene diphosphate into phytoene. Similarly, squalene synthetase in the presence of $Mg^{2+}$ and a reduced pyridine nucleotide, forms squalene by a two step reductive condensation of two molecules of farnesyl diphosphate.

Pyrethroid refers to a non-naturally occurring insecticidal compound chemically similar to a pyrethrin molecule. Some of the earliest pyrethroids chemically synthesized were simply substituted benzyl esters of chrysanthemic acid having insecticidal activity, for example, 4-allylbenzyl chrysanthemate. In 1965, the ester of chrysanthemic acid and 5-benzyl-3-furylmethyl alcohol, named resmethrin, was synthesized and found to be about twenty times as active as pyrethrin I against houseflies. Bioresmethrin, (+)-trans-resmethrin, is the most active of several isomers that make up the mixture constituting resmethrin. Bioresmethrin is twice as active as resmethrin and about fifty times as active as DDT [1,1,1-trichloro-2,2-bis-(p-chloro-phenyl)ethane] against houseflies.

In the 1970s three pyrethroids, permethrin, cypermethrin and decamethrin (deltamethrin), were chemically synthesized and were found to have high stability and high intrinsic insecticidal activity. These compounds were produced by varying the alcohol moiety and adding halogen substituents onto the side chains of the chrysanthemic acid part of the molecule. Introducing an α-cyano group approximately trebled the activity, which was further enhanced with dihalovinyl substituents and the side chain cis rather than trans to the ester group. These early beginnings in the synthesis of active pyrethroids quickly led to much competition in the search for new pyrethroids and many companies now have research and development programs in this field.

The currently available methods for the synthesis of pyrethroids generally produce mixtures of all possible isomers, each of which has a different level of biological activity. Usually, the product is marketed as a racemic mixture. Additionally, the different isomers are separated to varying extents depending on the resolution capability of the available technology, and the resolved forms of a pyrethroid are also marketed. Only in one case is a pyrethroid commercially available as a single active isomeric species. For example, deltamethrin is the only pyrethroid, to date, that is marketed as a single isomer, i.e., the most active D-cis isomer.

SUMMARY OF INVENTION

The present invention provides for the first time a purified chrysanthemyl diphosphate synthase (CDS) active in catalyzing the conversion of dimethylallyl pyrophosphate (DMAPP) to chrysanthemyl diphosphate (also called chrysanthemyl pyrophosphate). The purified enzyme has a molecular weight of approximately 40,000 daltons under both native and dissociating conditions and, hence, appears to be active in a monomeric form. The N-terminal amino acid sequence of isolated CDS is presented in Table 2, SEQ ID NO: 1.

The invention also provides a method useful in the purification of chrysanthemyl diphosphate synthase. In accordance with a specific embodiment of the invention, the enzyme was isolated from *Chrysanthemum cinerariaefolium*. The CDS enzyme may also be isolated from other chrysanthemol-producing or pyrethrin-producing Chrysanthemum, Artemisia, Santolina, Anacyclus or Tagetes species of the family Compositae. The CDS enzyme is purified to a level equal to at least approximately 1,000-fold enhancement with respect to total enzyme activity.

It is an object of the present invention to provide a DNA fragment encoding an amino acid sequence of chrysanthemyl diphosphate synthase. In a specific embodiment of the invention, cDNA encoding the CDS protein of *C. cinerariaefolium* and DNA recombinant vectors containing said cDNA are provided. A nucleotide sequence of the cDNA encoding the CDS protein is also provided. In a further embodiment of the invention, genomic DNA encoding the CDS protein of *C. cinerariaefolium* and recombinant vectors containing said genomic DNA are provided.

It is also an object of the invention to provide a host cell (for example, yeast, bacteria, etc.) transformed with DNA recombinant vectors comprising DNA encoding CDS protein and capable of producing the metabolic product of the CDS enzymatic reaction. For example, the product of CDS enzymatic activity in a host cell is chrysanthemyl diphosphate which is subsequently cleaved by host phosphatases to yield chrysanthemyl alcohol. Both chrysanthemyl diphosphate and chrysanthemyl alcohol have the correct stereochemistry of the native isomer found in Chrysanthemum species, i.e., having a (+)-trans-configuration.

It is a further object of this invention to provide a method of pyrethrin synthesis utilizing a combination of biological and chemical steps for the production of pyrethrins. A biosynthetic method of pyrethrin synthesis utilizes CDS enzyme activity produced by the instant invention to provide the stereochemically correct isomer [(+)-trans-isomer] of chrysanthemyl diphosphate and its corresponding alcohol and acid as substrates for further chemical synthesis of pyrethrin molecules. In a particular embodiment of this invention, a recombinant-synthetic method of pyrethrin synthesis utilizes a chrysanthemyl diphosphate synthase (CDS)-encoding DNA fragment transformed into a host cell, e.g., yeast, bacteria, etc., capable of expressing the DNA so that the expressed CDS activity produces (+)-trans-chrysanthemyl diphosphate which is then used to synthesize pyrethrins and derivatives thereof.

The present invention also contemplates providing a method for the synthesis of (+)-trans-pyrethroids utilizing a combination of biological and chemical steps. This method of pyrethroid synthesis utilizes CDS enzyme activity produced by the instant invention to provide the stereochemically correct isomer [(+)-trans-isomer] of, for example, chrysanthemyl diphosphate and its corresponding alcohol and acid as substrates for further chemical synthesis of pyrethroid molecules. In a specific embodiment of this invention, a recombinant-synthetic method of pyrethroid synthesis utilizes a DNA fragment encoding CDS transformed into a host cell capable of expressing the DNA so that the expressed CDS activity produces (+)-trans-chrysanthemyl diphosphate which is then used to synthesize a desired pyrethroid. This invention provides a method for producing a single pyrethroid isomer.

It is also contemplated in the present invention to provide a method for the synthesis of a (+)-trans-isomer of a substrate which is utilized for the synthesis of several classes of metabolites, including sterols, carotenoids, dolichols and ubiquinones. This method of metabolite synthesis utilizes CDS enzyme activity produced by the instant invention to provide the stereochemically correct isomer, i.e., (+)-trans-isomer. In a specific embodiment of this invention, a recombinant-synthetic method of metabolite synthesis utilizes a DNA fragment encoding CDS transformed into a host cell capable of expressing the DNA so that the expressed CDS activity produces a (+)-trans-isomer which is utilized to synthesize a desired metabolite.

It is also an object of the present invention to provide an antibody to CDS protein. Anti-CDS polyclonal and monoclonal antibodies bind specifically to CDS. Anti-CDS antibodies have utility, for example, as a diagnostic, e.g., in detecting successful transformation of cloned CDS in host cells or as a reagent, for example, in affinity chromatographic techniques for isolation and purification of CDS, etc.

It is a further object of the present invention to provide a reagent comprising the CDS protein of the invention which can be utilized, for example, in the production of pyrethrins, pyrethroids or intermediates thereof. Also, the CDS protein of the invention can be immobilized onto a resin matrix, e.g., DEAE-sephadex or phenyl sepharose, and used, for example, as a reagent catalyst for the production of pyrethrins and pyrethroids, or, as a ligand in affinity chromatography and used, for example, in the purification of corresponding antibodies.

BRIEF DESCRIPTION OF THE DRAWINGS

FIG. 4 presents a nucleotide sequence encoding the CDS protein isolated from *C. cinerariaefolium* and the derived amino acid sequence of the encoded CDS. A first met codon spans nucleotides 239–241; and the N-terminal amino acid sequence of the CDS protein of Table 2 corresponds to the nucleotide sequence between positions 389 and 448. The nucleotide sequence between positions 1217–1255 corresponds to the CDS tryptic peptide of peak 2 (Table 4); the sequence between positions 1265–1297 corresponds to the CDS tryptic peptide of peak 5 (Table 7); the sequence between positions 1301–1351 corresponds to the CDS tryptic peptide of peak 6 (Table 8); and the sequence between positions 1355–1390 corresponds to the CDS tryptic peptide of peak 4 (Table 5).

FIG. 5 presents an elution profile from HPLC hydroxyapatite chromatography and shows purification to homogeneity of a 40,000 dalton protein in SDS-PAGE.

DETAILED DESCRIPTION OF THE INVENTION

Figure 1:
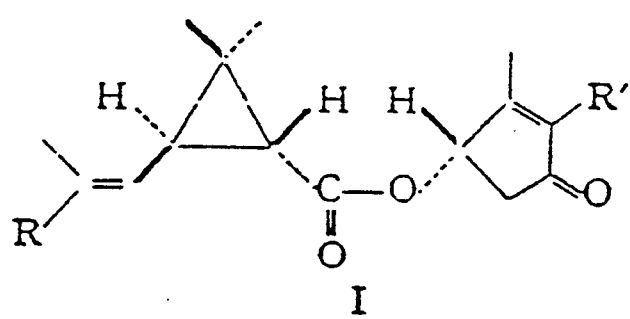
FIG. 1 illustrates the chemical structures of pyrethrin molecules.
Figure 2:
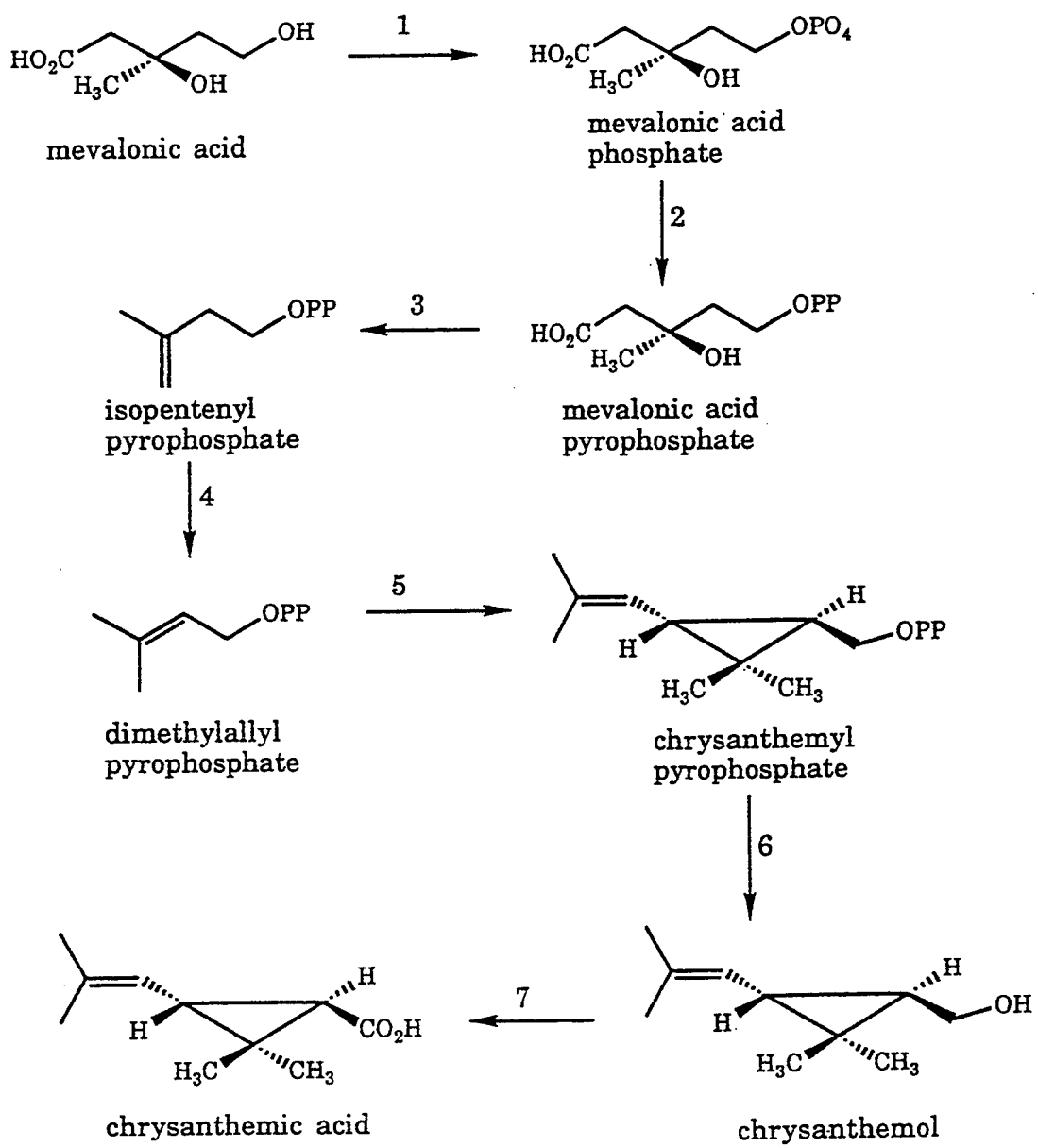
FIG. 2 presents a scheme for the biosynthesis of chrysanthemic acid.

The following definitions are provided in order to provide clarity as to the intent or scope of their usage in the specification and claims.

The term chrysanthemyl diphosphate synthase (CDS) as used herein refers to an enzyme capable of catalyzing the conversion of two molecules of dimethylallyl pyrophosphate to (+)-trans-chrysanthemyl diphosphate (also called chrysanthemyl pyrophosphate).

The term chrysanthemyl diphosphate synthase activity as used herein refers to the enzymatic conversion of two molecules of DMAPP to (+)-trans-chrysanthemyl diphosphate.

The term a purified chrysanthemyl diphosphate synthase (CDS) as used herein refers to a purified chrysanthemyl diphosphate synthase characterized by a purification level of at least approximately 100 fold, and preferably approximately 500 fold, with respect to total enzyme activity, a molecular weight of approximately 40,000 daltons in denaturing polyacrylamide gel electrophoresis (SDS-PAGE), and movement as a single peak in hydroxyapatite high performance liquid chromatography (HPLC-HA).

The term hybridize under stringent conditions as used herein refers to hybridization carried out under optimal reaction conditions of temperature, ionic strength and time of reaction which permit selective hybridization between oligomers and eliminate nondiscriminate hybridization. In a preferred embodiment of the invention, hybridization was carried out overnight at a temperature of 49° C. in 6x SSC medium with 0.5% sodium dodecyl sulfate (SDS), followed by three approximately ten-minute washes at 45° C. in 6x SSC medium with 0.1% SDS.

The term SSC medium as used herein refers to a solution consisting essentially of sodium chloride and sodium citrate. IX SSC medium refers to a solution containing 0.15M sodium chloride and 0.01M sodium citrate.

The term recombinant-synthetic method of producing pyrethrins as used herein refers to a method of synthesizing pyrethrin molecules combining art-known chemical reactions for the oxidation, esterification, etc., of substrate molecules with recombinant molecular biology techniques for the expression of the chrysanthemyl diphosphate synthase gene to produce enzymatically the correct stereoisomer of chrysanthemyl diphosphate.

The term biosynthetic method of producing pyrethrins as used herein refers to a method of synthesizing pyrethrin molecules combining art-known chemical reactions for the oxidation, esterification, etc., of substrate molecules with the step of using a chrysanthemyl diphosphate synthase enzyme to produce enzymatically the correct stereoisomer of chrysanthemyl diphosphate.

The term pyrethroid as used herein refers to a non-naturally occurring insecticidal compound chemically related to a naturally occurring pyrethrin compound present in flowers of various Chrysanthemum species. A key structural feature of a pyrethroid is the cyclopropane ring.

The term (+)-trans-pyrethroid as used herein refers to a pyrethroid structure comprising a (+)-trans-chrysanthemyl moiety or a derivative thereof.

The term biochemical reagent composition as used herein refers to a composition comprising chrysanthemyl diphosphate synthase useful as a reagent for the purification, detection, analysis or use as a substrate or intermediate in synthetic, biochemical or immunological reactions.

Chrysanthemyl diphosphate synthase (CDS) catalyses the condensation of two molecules of dimethylallyl pyrophosphate (DMAPP) to chrysanthemyl diphosphate. Although chrysanthemic acid may exist as four stereoisomers due to the two asymmetric carbon atoms in the cyclopropane ring structure, the natural isomer has the (+)-trans configuration. The enzyme catalyzed reaction converting DMAPP to chrysanthemyl diphosphate produces the isomeric form of the product having the correct stereochemistry. The CDS protein as isolated in the present invention was found to have a molecular weight of approximately 40,000 daltons in both dissociating and undissociating conditions. The enzyme was biologically active in its monomeric form. The enzyme can be isolated from various species of Chrysanthemum, e.g. *cinerariaefolium, coccineum, balsamita,* etc., as well as from other pyrethrin-producing genera of the family Compositae.

Purified chrysanthemyl diphosphate synthase has not been reported in the prior art. From the work of Zito and Staba, U.S. Pat. No. 4,525,455, it was indicated that the enzymes forming chrysanthemyl diphosphate and other enzymes involved in pyrethrin formation are cytosolic, since essentially all activity was found in the 100,000 X g supernatant and little to no activity was observed in the protoplastid and mitochondrial fractions. In the purification scheme of Table 1 and as detailed in Example 1, the cytosolic compartmentation of CDS is confirmed, particularly since polyvinylpyrrolidone was added to the extraction medium in order to stabilize whole cell integrity [Leibovitz et al. (1986) Cancer Genet. Cytogenet. 19:11–19]. Under these conditions, essentially all of the CDS enzymatic activity was found in the supernatant fraction.

In a specific embodiment of the invention, flower buds of *C. cinerariaefolium* were extracted with a Tris Cl [2-amino-2-(hydroxymethyl)-1,3-propanediol chloride] buffer at pH 7.6 comprising ascorbate, sucrose, magnesium ions, $\beta$-mercaptoethanol, serine protease inhibitor and polyvinylpyrrolidone.

TABLE 1

Purification of chrysanthemyl diphosphate synthase (CDS)

| Fractions | Total Protein (mg) | Units | Specific Activity (units/mg protein) | Purification (fold) |
|---|---|---|---|---|
| Crude | 211 | 84 | 0.4 | 0 |
| 30–55% NH4SO4 precipitate | 109 | 153 | 1.4 | 3 |
| DEAE Chromatography | 6 | 53 | 8.9 | 20 |
| Phenyl Sepharose Chromatography | 0.17 | 7.7 | 45.5 | 100 |
| HPLC DEAE Chromatography | 0.02 | 0.34 | 17.1* | 430 |
| HPLC Hydroxyapatite Chromatography | 0.006 | 0.09 | 14.5 | 1,100 |

One unit of activity is defined as the amount of enzyme which produces 1 pmol of chrysanthemyl diphosphate in 1 minute. For assay by gas chromatography (GC) the chrysanthemyl diphosphate is converted to chrysanthemyl alcohol using alkaline phosphatase.
*Specific activity of the enzyme preparation diminishes upon storage between phenyl sepharose and subsequent HPLC steps (DEAE and Hydroxyapatite) and also during HPLC. The specific activity reported herein is the specific activity determined after passage through the column. Fold purification is calculated based on assay of material immediately prior to column chromatography and comparing with total activity eluted from the column.

Homogenization was carried out by mechanical means such as mortar-and-pestle, homogenizer or blender or by nonmechanical means known in the art until a smooth paste was attained. CDS can also be extracted from leaves and shoots of *C. cinerariaefolium* and related Compositae plants and from tissue culture suspensions thereof. Polyvinylpyrrolidone was a preferred additive to prevent phenolic compounds from inhibiting CDS activity, although glycerol or other polyols can also be used. Phenylmethylsulfonyl fluoride was used preferentially to inhibit proteolytic action of proteases on solubilized proteins, although other known specific or general inhibitors e.g., EDTA, EGTA, benzamidine, pepstatin A, leupeptin, Aprotinin, Antipain, etc., can also be utilized. A thiol-reducing agent was added to prevent oxidation of sulfhydryl groups critical for biological activity. Dithiothreitol (DTT) was the preferred reagent, but other thiol compounds known in the art, e.g., dithioerythreitol, 2-mercaptoethanol, glutathione, etc., can also be utilized. $Mg^{2+}$ was identified as being a cofactor for the enzymatic activity of CDS; $Mn^{2+}$ and $Zn^{2+}$ could replace $Mg^{2+}$ as the cofactor in the enzyme reaction but were found to be not as effective as $Mg^{2+}$.

The first purification step was achieved by salt induced protein precipitation with neutral or slightly acidic salts, for example, NaCl, $Na_2SO_4$ and preferably $(NH_4)_2SO_4$. In a preferred embodiment of the invention, the CDS enzyme was concentrated in a 30–55% ammonium sulfate fraction. This $(NH_4)_2SO_4$ fraction accounted for all of the enzymatic activity; the original amount of enzyme activity appeared to be underestimated in the crude homogenate.

Purification on ion-exchange chromatography yielded a CDS preparation with a specific activity of approximately 9 units per mg protein (see Table 1). Additional purification on hydrophobic interaction (phenyl sepharose) chromatography yielded a CDS enzyme preparation enriched approximately 100-fold as compared to the enzyme activity of the crude homogenate. The phenyl sepharose fraction exhibiting a specific activity of approximately 45 units per mg protein showed two protein bands of approximately 40,000 daltons in SDS-PAGE gels. This 40,000 dalton protein "doublet" eluted from the electrophoretic gel gave the N-terminal amino acid sequence SEQ ID NO:1 (Table 2).

TABLE 2

| N-terminal amino acid sequence of CDS after phenyl sepharose chromatography* (SEQ ID NO: 1) |
|---|
| thr-thr-thr-leu-ser-ser-asn-leu-asp-ser-gln-phe-met-gln-val-tyr-glu-thr-leu-lys |

*Followed by SDS PAGE purification and extraction of the protein from the gel.

Many ion-exchange and hydrophobic resins are known in the art and can be used as alternative matrices for the chromatographic purification steps (see, for example, Rossomondo (1990) Methods in Enzymol. 182:309–317 and Kennedy (1990) Methods in Enzymol. 182:339–343). The chromatographic steps resulted in a loss of total units of enzymatic activity. The apparent instability of the enzyme, appearing as inactivation of enzyme activity, may result in protein degradation, as suggested by the manifestation of two protein bands differing by only about 2000 daltons on SDS gel electrophoresis in the purified fraction. Inhibitors of various plant proteases known in the art can be added to the extraction medium to prevent protein degradation during the purification procedure.

Further purification of the CDS was carried out on HPLC ion exchange chromatography and HPLC adsorption chromatography. In a preferred embodiment of the invention, HPLC-DEAE chromatography was followed by HPLC-hydroxyapatite (HA); however, many different ion exchange and adsorption resins are available in the art and alternative matrices can be used at any protein purification step [see, for example, Rossomando (1990) Methods in Enzymology 182:309–317; Gorbunoff (1990) Methods in Enzymology 182:329–339; and Chicz and Regnier (1990) Methods in Enzymology 182:392–421]. In a preferred embodiment of the invention, the combined chromatographic procedures resulted in an approximately 1,100-fold increase in level of purification, a single protein band on SDS-PAGE having an apparent molecular weight of 40,000 daltons, movement as a single peak on HPLC-hydroxyapatite chromatography and the N-terminal amino acid sequence SEQ ID NO:2 as shown in Table 3. The single protein band on SDS-PAGE observed for the HPLC-HA purified CDS corresponded to the lower band of the "doublet" protein bands observed for the phenyl sepharose fraction. The N-terminal amino acid sequence observed for the HPLC-HA purified CDS (SEQ ID NO:2; Table 3) corresponded almost identically to that obtained for the phenyl sepharose purified CDS (SEQ ID NO:1; Table 2).

TABLE 3

| N-terminal amino acid sequence of CDS after HPLC-HA chromatography (SEQ ID NO: 2) |
|---|
| thr-thr-thr-leu-ser-ser-asn-leu-asp-Xaa-gln-phe-Xaa-gln |

Xaa = residues which could not be identified with certainty.

The HPLC-HA purified CDS protein, subjected to trypsin digestion followed by HPLC, yielded five tryptic fragments which were subjected to amino acid sequencing. The amino acid sequences for various tryptic fragments of CDS are presented in Tables 4–9. The CDS tryptic fragment in peak 2 yielded the thirteen-amino acid sequence presented in Table 4.

TABLE 4

| Amino acid sequence of the tryptic fragment of CDS in peak 2 (SEQ ID NO: 3) |
|---|
| ile-leu-ser-glu-asn-tyr-gly-ile-asn-asp-pro-ser-lys |

Amino acid residue in position 3 has not been identified definitively.

An eight amino acid fragment having a sequence corresponding to that of trypsin was found as a minor component in peak 2. Peak 3 did not produce a viable signal.

Peak 4 comprised two components; the major component [peak (a)] possessed the twelve-amino acid sequence of Table 5, whereas the minor component [peak 4(b)] had the seven amino acid sequence presented in Table 6.

TABLE 5

| Amino acid sequence of the tryptic fragment of CDS in peak 4 (a) (SEQ ID NO: 4) |
|---|
| ala-his-pro-asn-ile-ala-val-gln-ala-val-leu-lys |

TABLE 6

Amino acid sequence of the
tryptic fragment of CDS in peak 4 (b)
(SEQ ID NO: 5)

Xaa-leu-tyr-his-ala-leu-asp

Xaa = residue which could not be identified with certainty.

The CDS tryptic fragment in peak 5 yielded the eleven-amino acid sequence of Table 7.

TABLE 7

Amino acid sequence of
the tryptic fragment of CDS in peak 5
(SEQ ID NO: 6)

Val-lys-glu-leu-tyr-his-ala-leu-asp-leu-lys

Amino acid residue in position 2 has not been identified definitively.
Amino acid residue in position 3 is either gly or glu.

The six-amino acid sequence identified in peak 4(b) (minor component) is identical to the sequence from positions 4 to 9 determined for peak 5 and, most probably, defines a common region within overlapping tryptic fragments. The fragment in peak 6 gave the eighteen-amino acid sequence of Table 8, while peak 7 contained a tryptic fragment having the eleven-amino acid sequence presented in Table 9.

TABLE 8

Amino acid sequence of the
tryptic fragment of CDS in peak 6
(SEQ ID NO: 7)

Xaa-ala-tyr-glu-asp-tyr-glu-thr-asn-leu-tyr-glu-thr-ser-met-thr-ser-ile

Xaa = residue which could not be identified with certainty.
Amino acid residues specified in positions 2 and 17 have not been identified definitively.
Amino acid residue in position 3 is either tyr or ser.
Amino acid residue in position 4 is either glu or gly.

TABLE 9

Amino acid sequence of the
tryptic fragment of CDS in peak 7
(SEQ ID NO: 8)

Xaa-ala-tyr-glu-asp-tyr-glu-ser-asn-glu-tyr

Xaa = residue which could not be identified with certainty.

The ten-amino acid sequence determined for the component in peak 7 was similar to the sequence obtained for the component in peak 6, from positions 2 to 11, excluding positions 8 and 9.

In a specific embodiment of the invention, the properties of the chrysanthemyl diphosphate synthase from *C. cinerariaefolium* were examined in a protein fraction purified with phenyl sepharose chromatography. $Mg^{2+}$ was found to be a cofactor in the enzyme reaction. The optimum concentration of $MgSO_4$ was 3 to 5 mM. Other divalent metal ions, such as $Mn^{2+}$ and $Zn^{2+}$, could be used as cofactors, but these gave lower CDS activity compared to that with $Mg^{2+}$. Iodoacetamide was found not to inactivate chrysanthemyl diphosphate synthase activity, suggesting that active-site sulfhydryl groups are not critical for enzyme activity. This feature provided an advantage in assaying for chrysanthemyl diphosphate activity wherein isopentenyl pyrophosphate (IPP) isomerase which competes for DMAPP can be inhibited with iodoacetamide. The temperature optimum for maximum enzyme activity was about 30° to 32°C. and the optimum Ph was found to be about 7.8.

A DNA fragment encoding the chrysanthemyl diphosphate synthase (CDS) of the invention was obtained using information from a partial amino acid sequence of the CDS protein, [Wood (1987) Methods in Enzymology 152:443–447 and Matsudaira (1990) Methods in Enzymol. 182:602–613]. This approach has been described for the isolation and identification of a sequence from a tomato cDNA library [King et al. (1988) Plant Mol. Biol. 10:401-412]. From the amino acid sequence information, corresponding short (11–20 nucleotides) or long (30–100 nucleotides) oligonucleotide probes are synthesized using known methods of chemical synthesis of nucleic acids and, preferably, using the phosphoramidite method with an Applied Biosystems DNA synthesizer [Matteucci et al. (1981) J. Am. Chem. Soc. 103:3185; Beaucage et al. (1981) Tetrahedron Lett. 22:1859; and Hill et al. (1989) Recombinant DNA Methodology, Wu, et al. (eds.), Academic Press, pp. 622–623]. Several different oligonucleotides corresponding to different regions of the amino acid sequence are synthesized. Preferably, oligonucleotides having between about 15 and about 30 nucleotides are utilized as hybridization probes. Because of the redundancy of the genetic code, there are numerous possibilities for the actual nucleotide sequence. Since oligonucleotides hybridize to their complementary sequence with a high degree of specificity and since only those duplexes in which all of the nucleotides are base-paired will be formed, multiple oligonucleotide probes with mixed bases at particular positions or with inosine at degenerate positions [Ohtsuka et al. (1988) J. Biol. Chem. 260:2605–2608] are used. In a specific embodiment of the invention, an oligonucleotide probe was synthesized commercially (Genosys Biotechnologies, Inc., The Woodlands, Tex.) to contain codons corresponding to the region of least degeneracy, i.e., residue 11-18 of SEQ ID NO:1 (Table 2). The nucleotide sequence of the synthesized oligonucleotide probe is given in Table 10 (SEQ ID NO:9). The twenty-three nucleotide-long sequence contains one inosine base, has a 32-fold redundancy and an approximate min. $T_M = 54°$ C.

TABLE 10

Nucleotide sequence of the synthetic oligonucleotide probe
(SEQ ID NO: 9)

5' - CAR TTY ATG CAR GTI TAY GAR AC - 3'

Y = T or C; R = A or G

A cDNA library was constructed from immature *C. cinerariaefolium* flower mRNA, according to the procedures outlined by Kimmel and Berger (1987) Meth. Enzymol. 152:307–359. In one embodiment of the invention, cDNA was synthesized from polyA enriched RNA using Stratagene Zap cDNA synthesis kit. The cDNA was cloned into the Stratagene Lambda Zap vector. The nucleotide sequence (SEQ ID NO:10) of the cDNA encoding the CDS protein is presented in FIG. 4. The sequence from position 389 to position 448 comprises the portion of the gene encoding the N-terminal region of the CDS protein as shown in Table 2. The nucleotide sequence between positions 1217 and 1255 of the gene corresponds to CDS tryptic peptide of peak 2 (Table 4); the nucleotide sequence between positions 1265 and 1297 corresponds to CDS tryptic peptide of peak 5 (Table 7); the nucleotide sequence between positions 1301 and 1351 corresponds to CDS tryptic peptide of peak 6 (Table 8); and the nucleotide sequence between positions 1355 and 1390 codes for tryptic peptide of peak 4 (Table 5 ).

As is well known in the art [see, for example, Glover (1984) *Gene Cloning*, Brammar and Edidin (eds.), Chapman and Hall, NY], there are other strategies for generation of cDNA libraries and for the cloning of the cDNA into an appropriate DNA recombinant vector, e.g., the pUC family of plasmids or λgt10 or λgt11 phage vectors. In a specific embodiment of the invention, a DNA recombinant vector carries a bacteriophage promoter adjacent to the cloning site such that a transcript is made specifically to either strand of the cDNA simply by using different RNA polymerases. RNAs produced in this way can be used as hybridization probes or can be translated in cell-free protein synthesis systems.

It is understood in the art that modifications may be made to the structural arrangement and specific elements of a genetically-engineered recombinant DNA molecule described herein without destroying the activity of gene expression. For example, it is contemplated that a substitution may be made in the choices of enhancer regulatory elements and/or promoters (e.g., preferably, a constitutive promoter) without significantly affecting the function of the recombinant DNA molecule of this invention. It will also be understood that optimization of gene expression also results from the arrangement, orientation and spacing of the different regulatory elements as well as the multiple copies of a particular element with respect to one another, and with respect to the position of the TATA box, as will be apparent to those skilled in the art using the teachings of this disclosure.

In a preferred embodiment of the invention, the cDNA library was screened with the labelled synthetic oligonucleotide probe derived from the N-terminal CDS protein sequence. In an alternative embodiment of the invention, individual recombinants within the cDNA library can be screened for expression of an antigen (antibody recognition) or for expression of a phenotype (i.e., enzyme activity). The procedure for selecting cloned sequences from a recombinant cDNA library is described in Kimmel (1987) Meth. Enzymol. 152:393–399.

cDNA clones which show a strong hybridization signal are sequenced to confirm complimentarity to the CDS amino acid sequence. In addition, the protein encoded by the cDNA is shown to possess the enzymatic activity to convert DMAPP to chrysanthemyl diphosphate. This is done, for example, by transcribing the clone sequence with an appropriate RNA polymerase, then translating the mRNA in a commercially available rabbit reticulocyte lysate or wheat germ extract in vitro translation system.

In another embodiment of the invention, the presence of CDS protein was detected immunologically. For example, antibodies raised to a CDS protein purified and isolated from a SDS-PAGE gel were shown to cross-react with the purified 40,000 dalton CDS protein. CDS-specific antibodies are also utilized to inactivate and precipitate CDS activity from plant extracts as well as the product of the cloned CDS gene. Polyclonal and monoclonal antibodies specific to CDS protein are prepared according to standard methods in the art. This type of immunological testing is further utilized, for example, for optimization of expression of the cloned CDS gene in a recipient organism.

This invention further contemplates the isolation of a genomic clone of CDS. Genomic DNA is isolated according to the methods described by Herrmann and Frischauf (1987) Methods Enzymol. 152:180–189. A PCR-based method is used to clone a gene from genomic DNA using partial protein sequence [e.g., Aarts et al. (1991) Plant Mol. Biol. 16:647] or cDNA fragment probes [e.g., King et al. (1988) Plant Mol. Biol. 10:401–412]. The genomic CDS gene may be utilized instead of the cDNA to express CDS, in particular in host systems where it appears that the native 5′ system is required for full expression of enzymatic activity.

It is an object of the instant invention to produce enzymatically chrysanthemyl alcohol to serve as substrate for the chemical synthesis of pyrethrin. One of the most expedient ways to produce chrysanthemyl alcohol is to introduce the clone which encodes chrysanthemyl diphosphate synthase (CDS) into an expression system, for example, yeast, bacteria (*E. coli, B. subtilis*, etc.), which would generate the desired alcohol. For example, industrial yeast is amenable to genetic transformation using dominant selectable markers. Preferably, yeast is selected for (a) low or no catabolic activity of chrysanthemyl alcohol, (b) the ability to cleave chrysanthemyl diphosphate to the corresponding alcohol, and (c) a strong ability to excrete the alcohol and to tolerate high levels of alcohol in the growth medium.

Chrysanthemyl diphosphate can be transformed into chrysanthemyl alcohol in yeast by different pathways. For example, yeast contains both an acid and an alkaline phosphatase which are associated with the vacuole. The alkaline phosphatase is reported to be a vacuolar membrane protein. The presence of a high concentration of chrysanthemyl diphosphate resulting from overproduction of this compound in transformed yeast cells allows chrysanthemyl diphosphate to be transported into the vacuole where it is enzymatically transformed into chrysanthemyl alcohol. In an alternate method, yeast is grown in limiting concentration of phosphate to induce the yeast cell to cleave phosphate from chrysanthemyl diphosphate in an effort to conserve phosphate. Alternatively, the chrysanthemyl diphosphate produced in yeast is isolated and subsequently converted chemically or biochemically in vitro to the corresponding alcohol.

Yeast transformation techniques are described in detail in the literature. Successful expression of various foreign proteins, including plant proteins, has been reported [Goodey et al. (1987) Yeast Biotechnology, Berry et al. (eds.), Allen and Unwin, pp. 401–429; Tague et al. (1987) J. Cell. Biol. 105:1971; Rothstein et al. (1984) Nature 308:662; Parent et al. (1985) Yeast 1:83]. The chrysanthemyl alcohol produced in yeast is used as a substrate for pyrethrin synthesis. The instant invention contemplates a method for isolating chrysanthemyl alcohol from fermentation broth, for example, a method comprising steam distillation. Although this method is favored, it is appreciated that other technology can be applied to the optimization of the production of primary or secondary metabolites and the subsequent recovery of the product or its derivative.

Figure 3:
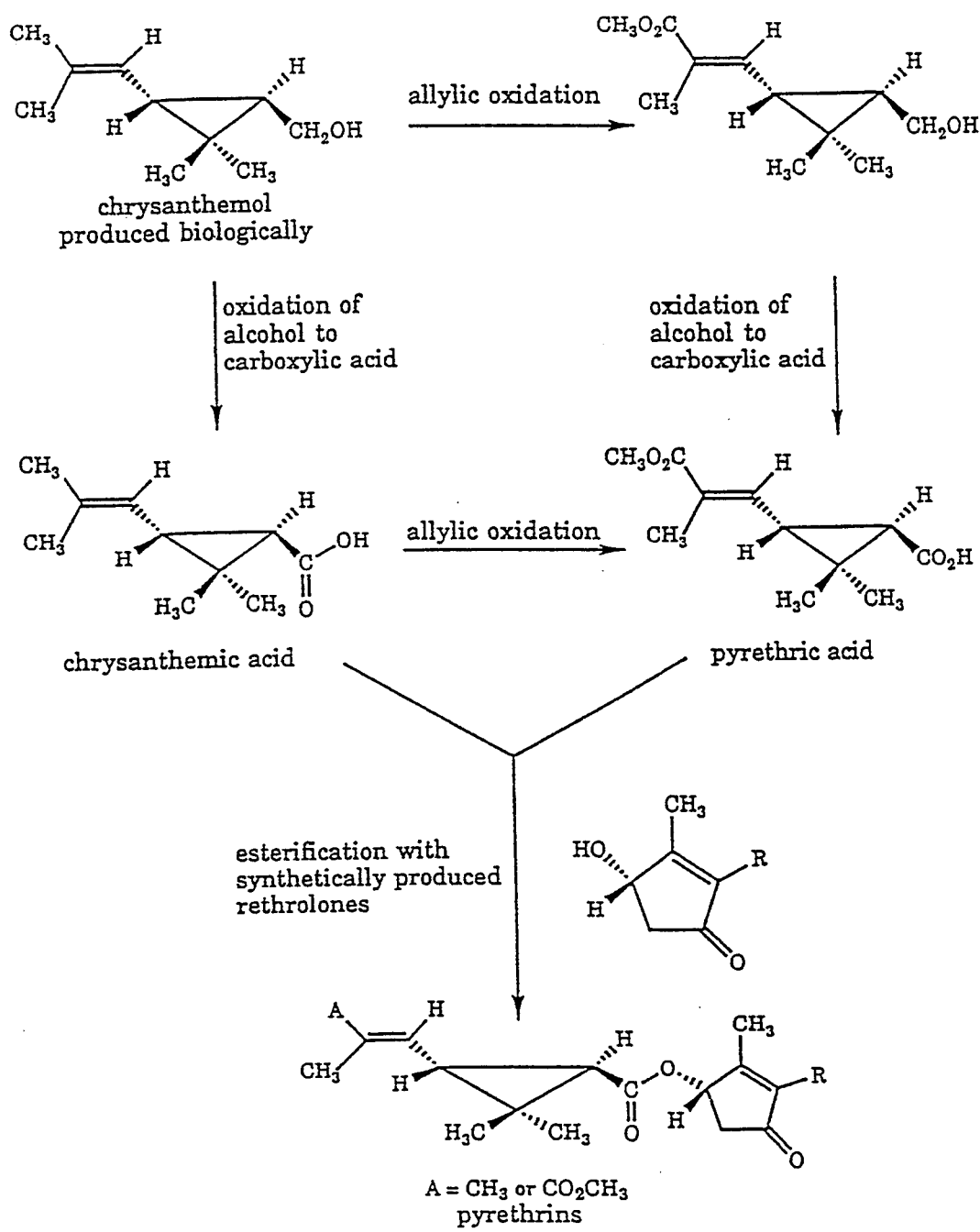
FIG. 3 presents a scheme for the combined chemical and biological preparation of pyrethrins.

It is further an object of the instant invention to synthesize pyrethrins utilizing the CDS gene of the invention in combination with known chemical synthetic reactions. Synthesis of the rethrolone moiety (hydroxycyclopentenone), the alcoholic component of the pyrethrin esters in *Chrysanthemum cinerariaefolium*, is performed according to known methods, for example, the highly efficient synthetic route to racemic rethrolones described by Romanet and Schlessinger (1974) J. Am. Chem. Soc. 96:3701; the synthetic procedures for preparation of high yields of starting materials described by Bradsher et al. (1954) *J. Am. Chem. Soc.* 76:114 and Herrmann et al. (1973) *Tetrahedron Lett.* 47:4707. As schematically outlined in FIG. 3, the rethrolone moiety is then esterified with chrysanthemic acid or pyrethric acid using art-known synthetic reactions to produce pyrethrin I or pyrethrin II. Pyrethrin derivatives, pyrethroids and pyrethroid derivatives are similarly synthesized following a strategy similar to that outlined in FIG. 3, when appropriate cyclopropyl and keto-alcohol moieties are selected for the desired pyrethrin or pyrethroid molecule.

The instant invention—the purified CDS enzyme and corresponding gene—enables the production of the correct stereoisomer of chrysanthemyl diphosphate which is then utilized as substrate for the chemical synthesis of pyrethrin molecules and derivatives thereof. Some of the reactions comprised in the overall synthetic procedure are outlined in FIG. 3. In a specific embodiment of the invention chrysanthemyl diphosphate is converted to chrysanthemyl alcohol which is oxidized to the corresponding acid in the presence of an oxidizing agent as described, for example, by Dalton et al. U.S. Pat. No. 4,225,694. This invention then contemplates the merging of chrysanthemic acid with rethrolone using esterification procedures known in the art. The resultant pyrethrin esters are interconverted using known oxidants and reaction conditions providing the highest yield under conditions amenable to large scale productions.

Except as noted hereafter, standard techniques for cloning, DNA isolation, amplification and purification, for enzymatic reactions involving DNA ligase, DNA polymerase, restriction endonuclease and the like, the PCR technique and various protein separation and purification techniques are those known and commonly employed by those skilled in the art. A number of standard techniques are described in Maniatis et al. (1982) *Molecular Cloning*, Cold Spring Harbor Laboratory, Cold Spring Harbor, N.Y.; Wu (ed.) (1979) Meth. Enzymol. 68; Sambrook, et al. (1989) *Molecular Cloning: A Laboratory Manual*, Second Edition, Cold Spring Harbor Press, N.Y.; Wu et al. (1983) Meth. Enzymol. 100 and 101; Grossman and Moldave (eds.) (1980) Meth. Enzymol. 65; Miller (ed.) (1972) *Experiments in Molecular Genetics*, Cold Spring Harbor Laboratory, Cold Spring Harbor, N.Y.; Old and Primrose (1981) *Principles of Gene Manipulation*, University of California Press, Berkeley; Schleif and Wensink (1982) *Practical Method of Molecular Biology;* Glover (ed.) (1985) *DNA Cloning* Vol I and II, IRL Press, Oxford, UK; Hames and Higgins (eds.) (1985) *Nucleic Acid Hybridization*, IRL Press, Oxford UK; Setlow, Hollaender (1979) *Genetic Engineering: Principles and Methods*, Vols. 1–4, Plenum Press, New York and Deutscher (ed.) (1990) *Guide to Protein Purification*, Academic Press, New York. Abbreviations and nomenclature, where employed, are deemed standard in the field and commonly used in professional journals such as those cited herein.

It will be appreciated by those of ordinary skill in the art that the objects of this invention can be achieved without the expense of undue experimentation using well known variants, modifications, or equivalents of the methods and techniques described herein. The skilled artisan will also appreciate that alternative means, other than those specifically described, are available in the art to achieve the functional features of the recombinant molecules described herein and how to employ those alternatives to achieve functional equivalents of the recombinant molecules of the present invention. It is intended that the present invention include those variants, modifications, alternatives and equivalents which are appreciated by the skilled artisan and encompassed by the spirit and scope of the present disclosure.

The following examples are provided for illustrative purposes only and are not intended to limit the scope of the invention.

EXAMPLE 1:

Purification of Chrysanthemyl Diphosphate Synthase (CDS)

(a) Assay for CDS Enzymatic Activity

Chrysanthemyl diphosphate synthase (CDS) catalyzes the conversion of two molecules of dimethylallyl pyrophosphate (DMAPP) to chrysanthemyl diphosphate. CDS activity was determined by gas chromatographic (GC) analysis of chrysanthemyl alcohol prepared by the conversion of DMAPP to chrysanthemyl diphosphate with subsequent cleavage to chrysanthemyl alcohol. Since DMAPP was not available commercially, it was synthesized according to the method of Poulter et al. as described in Example 6. The conversion of DMAPP to chrysanthemyl diphosphate was conducted in a 1 ml volume containing the following components: 100 mM Tris-HCl pH 7.8, 0.5 mM DTT, 3 mM $MgSO_4$, 1 mM DMAPP and an aliquot of enzyme. During the early steps of the purification procedure, 1 mM iodoacetamide was also included in the reaction mixture to inhibit isopentenyl diphosphate isomerase activity. Incubation time was 15 to 30 minutes or more (depending on the level of activity) at 31° C., followed by 5 minutes of boiling to stop the reaction.

Conversion of chrysanthemyl diphosphate to chrysanthemol was effected by adjusting the pH of the boiled assay solution by addition of 200 μl of 0.5M glycine pH 10.4 plus 24 μl 50 mM $ZnCl_2$. Approximately 400 units of alkaline phosphatase were then added and the reaction mixture incubated for 15 minutes at 37° C. Following the incubation with alkaline phosphatase, 0.3 ml of saturated NaCl solution and 0.2 ml of methylene chloride were added to each assay tube. The tubes were vortexed for 30 seconds and centrifuged to clarify the organic layer. Then 4 μl of the methylene chloride solution was injected onto an FFAP (Alltech) gas chromatographic column at 135° C. Chrysanthemyl alcohol levels were quantitated by comparing peak areas with an R-trans-chrysanthemyl alcohol standard curve.

The only cofactor that has been identified for the enzyme is $Mg^{2+}$. The optimum concentration of $MgSO_4$ is 3 to 5 mM. Other metals, such as $Mn^{2+}$ and $Zn^{2+}$ have been examined and these gave lower CDS activity compared to that with $Mg^{2+}$. The temperature optimum for maximum activity is 30° to 32° C. and the optimum pH is approximately 7.8.

(b) Purification Scheme

1. PLANT MATERIAL

Plants of *Chrysanthemum cinerariaefolium* were grown in a greenhouse maintaining a temperature of 15°–23° C. and 18 hour light/6 hour dark cycles. Seedlings were initially induced to flower by treatment at 4° C. for 6 weeks in a growth chamber followed by moving to the greenhouse. Subsequently, plants were encouraged to continue flowering by weekly harvesting of all flower buds and by division of the plants.

2. INITIAL EXTRACTION

Flower buds were harvested as the flower petals were beginning to emerge and expand, but, before the petals had fully emerged and dropped to a horizontal position. Stem material was removed and the buds were immediately placed on ice. Unless stated otherwise, subsequent extraction procedures were carried out at 4° C. Buds were ground in 5 ml of extraction buffer plus 0.4 g insoluble polyvinylpolypyrrolidone (PVP) per gram of buds. Extraction buffer consisted of 100 mM tris(hydroxymethyl)aminomethane (Tris), 100 mM ascorbic acid, 100 mM sucrose, 100 mM $\beta$-mercaptoethanol ($\beta$-ME), and 5 mM magnesium sulfate. Grinding was done in two steps with an initial coarse grinding for 30 seconds in a stainless steel blender followed by a 2 minute grinding with a Sorvall Tissue Mizer. Ground material was centrifuged for 15 minutes at 15,000×g in 250 ml or 500 ml polystyrene bottles in a Beckman JA-21 centrifuge. The supernatant was decanted and saved, and the pellet was extracted with an additional 50–100 ml of extraction buffer. The supernatant (centrifuged as above) was decanted and added to the first supernatant and the pellet was discarded. Combined supernatants were filtered through miracloth (Calbiochem). For each 20 ml of filtrate, 1 g of Cell Debris Remover (Whatman, Hillsboro, Oreg.) was added, mixed thoroughly, and allowed to sit without stirring for 10 minutes. The mixture was filtered through a Whatman 541 filter and the filtrate was saved.

3. AMMONIUM SULFATE PRECIPITATION

The extract described above was brought to 30% saturation with ammonium sulfate (molecular biology reagent grade, Sigma Chemical Co., St Louis, Mo.) by slowly adding ammonium sulfate over a 15 minute period. The 30% saturated solution was allowed to equilibrate with stirring for 30 minutes and then centrifuged at 15,000×g for 15 minutes in a Beckman JA-21 centrifuge. The pellet was discarded and the supernatant was filtered through miracloth. The supernatant was brought to 55% saturation with ammonium sulfate by slow addition of ammonium sulfate over 15 minutes and equilibration with stirring for 30 minutes. The 55% saturation solution was centrifuged at 15,000×g for 20 minutes in a Beckman JA-21 centrifuge. The supernatant was discarded and the pellet was retained for further purification. At this point, precipitated material could either be stored at −70° C. or could be used directly for further purification. Typically, 5 to 10 extractions were made and stored over a period of weeks and then the pellets from these extractions were thawed on ice, combined, and re-aliquoted to obtain about 300 mg of protein per aliquot (approximately 10–12 ml of slurry). These pools of protein were again stored at −70° C. and thawed just prior to further purification.

4. PREPARATIVE ANION EXCHANGE CHROMATOGRAPHY

Stored ammonium sulfate aliquots of approximately 300 mg protein were resuspended in imidazole buffer [20 mM imidazole, pH 7.0, 1 mM magnesium sulfate, 0.5 mM dithiothreitol (DTT)] to a total volume of 40 ml. The resuspended material was centrifuged in a Beckman L8-55 Ultracentrifuge equipped with an SW-28 rotor and operated at 22,000 rpm for 45 minutes. The supernatant was filtered through a 0.8 $\mu$m syringe adapted cellulose acetate filter.

Residual ammonium sulfate was removed from the filtrate by passing it through KWIK TM desalting columns (Pierce, Rockford, Ill.). For a 30 ml desalting column, 9 ml of filtrate was allowed to permeate the pre-equilibrated column and then 10 ml of buffer was applied to elute the protein fraction.

The desalted solution was brought to 75 mM NaCl with a solution of 5M NaCl and then applied to a 1.5×8 cm Econocolumn (Bio-Rad, Hercules, Calif.) which had been packed with Toyopearl DEAE-650M (Toso-Haas, Montgomerville, Pa.) and equilibrated with imidazole buffer with 75 mM NaCl. The protein was applied at a flow rate of 4 ml per minute. After loading the protein onto the column, it was washed, using the same flow rate, with imidazole buffer containing 75 mM NaCl until the absorbance at 280 nm was near baseline. Protein was then eluted with a 160 ml 75 mM to 200 mM NaCl gradient in imidazole buffer at a rate of 1 ml per minute.

Aliquots from each fraction were assayed to locate the CDS activity. Active fractions eluted at about 120 mM NaCl.

5. HYDROPHOBIC INTERACTION CHROMATOGRAPHY (HIC)

Active fractions (3 to 4 ml each) from preparative DEAE chromatography were individually brought to 2M NaCl by adding solid NaCl. The fractions were applied to 5 ml capacity, disposable polystyrene columns (Pierce) packed with 1 ml of Phenyl Sepharose CL-4B (Pharmacia, Piscataway, N.J.) slurry equilibrated with 2M NaCl in imidazole buffer. Protein was eluted by stepwise addition of 5 ml of 1.0M, 0.5M, 0.3M, 0.2M, and 0M NaCl in imidazole buffer. Peak activity eluted in the 0M wash.

At this point, enzyme could be stored by adding glycerol to 30% followed by storage at −20° C. or it could be used immediately for further purification.

Results from a typical extraction are given in Table 1. As indicated in Table 1, 60–70% of the activity is lost through the phenyl-sepharose step. The loss of activity is probably attributable to column selection and enzyme instability in specific column fractions.

The CDS protein was identified on SDS-PAGE gels. The native molecular weight of the CDS protein was determined to be 40,000±5,000 daltons, by comparing side and peak CDS active fractions from phenyl sepharose, hydroxyapatite and size exclusion chromatography which were also analyzed on SDS-PAGE gels. When the protein fraction obtained after phenyl sepharose chromatography was run on SDS-PAGE, a protein "doublet" was observed at the approximately 40,000 dalton position. The two proteins of the doublet were the only proteins from several experiments which consistently correlated with CDS activity. These two proteins separated distinctly on the SDS-PAGE gel, and differed in molecular weight by about 1,000–2,000 daltons.

6. HPLC ANION EXCHANGE CHROMATOGRAPHY (AX)

Active fractions from HIC, either fresh or stored, were applied to a 1×10 cm Protein-Pak TM DEAE 8 HR column (Waters, Milford, Pa.). In most cases, the protein had been stored in glycerol, so the initial flow rate in loading the column was adjusted to avoid exceeding the pressure limits of the column. For a typical HPLC run with protein that had been stored in glycerol, the following parameters were used. The column was equilibrated with 20 mM 2-bis[2-hydroxyethyl- ]amino-2-[hydroxymethyl]-1,3-propanediol (Bis-Tris) buffer, pH 6.3, with 5 mM magnesium sulfate, and 0.5 mM DTT. Protein was loaded onto the column at a flow rate of 0.5 ml per minute. At this flow rate the Absorbance at 280 nm had returned to baseline after approximately 20 minutes. A ten minute gradient to 100 mM NaCl in Bis-Tris and increasing the flow to 1.5 ml per minute was applied followed by a 50 minute linear gradient from 100 mM NaCl to 300 mM NaCl in Bis-Tris with no change in the flow rate. Using this procedure active fractions eluted at about 190 mM NaCl.

7. HPLC HYDROXYAPATITE CHROMATOGRAPHY (HA)

Active fractions from HPLC-AX were exchanged to 1 mM phosphate buffer, pH 6.8, with 5 mM magnesium sulfate and 0.5 mM DTT using KWIK ™ columns pre-equilibrated with phosphate buffer. Protein in 1 mM phosphate buffer was applied to a 4.0 mm ×7.5 cm Hydroxyapatite HCA-Column (Mitsui Toatsu, distributed by Rainin, Woburn, Mass.) equilibrated with 1 mM phosphate buffer. The flow rate was kept at 1.0 ml/minute throughout the procedure. The protein was eluted with a gradient consisting of 20 minutes of 1 mM phosphate followed by a linear gradient from 1 mM phosphate to 200 mM phosphate over 40 minutes. Using this procedure active fractions eluted at about 50 mM phosphate.

An elution profile is illustrated in FIG. 5, showing a correspondence between CDS activity and enrichment in the 40,000 dalton protein in the fractions comprised within the main elution peak. At this point, homogeneity, as determined by SDS-PAGE and reversed phase HPLC, had been achieved. A single protein was identified on the SDS-PAGE gels at the 40,000 dalton position. This single protein corresponded to the lower band of the protein "doublet" obtained from earlier purification steps.

(c) Tryptic Digestion of CDS

Approximately 100 pmoles of DEAE-HA purified CDS protein, dried from a volume of approximately 4 ml to approximately 100 μl, was made 20 mM in NH$_4$HCO$_3$. For digestion with trypsin, the CDS solution was made 4M in urea and 1.6 mM in DTT and heated at 70° C. for 15 minutes before addition of imidazole to a concentration of 5 mM, further incubation at room temperature for 15 minutes, followed by addition of 140 μl of H$_2$O. Trypsin (modified, sequencing grade, Promega, Madison, Wis.) was then added to give a concentration of 1.5 mg/ml and the mixture was incubated overnight at 37° C.

Tryptic fragments of CDS were purified using reversed phase HPLC (Waters 625LC System, 486 Absorbance detector, 625 pump). The tryptic digest was loaded onto a 2.1×250 mm column (Vydac C$_{18}$ Vydac Hesperia, Calif., catalog number 218TP52) and eluted at a flow rate of 0.15 μl/min in fractions collected at two tubes per minute. Elution was performed using a step gradient of mixtures of 0.1% trifluoroacetic acid in double distilled water (A) and 0.1% trifluoroacetic acid in 95% acetonitrile (B). Elution was begun with a mixture consisting of 96% A and 4% B, at 60 minutes the elution mixture was changed to 68% A and 32% B, at 90 minutes a mixture of 37% A and 63% B was used, and at 105 minutes the mixture contained 16% A and 84% B. The eluted material was monitored at 214 nm. The tryptic fragments were sequenced at the University of Utah Core facility using an Applied Biosystem 477A protein sequencer. The peaks described in Table 11 were analyzed and sequenced.

TABLE 11

| Tryptic fragments of CDS | | | |
|---|---|---|---|
| Reversed phase column | | | |
| Peak | Retention Time (min.) | Amino acid sequence SEQ ID | Table |
| 2 | 44.100 | NO: 3 | 4 |
| 4 (a) | 51.533 | NO: 4 | 5 |
| 4 (b) | 52.183 | NO: 5 | 6 |
| 5 | 53.717 | NO: 6 | 7 |
| 6 | 60.217 | NO: 7 | 8 |
| 7 | 62.033 | NO: 8 | 9 |

(d) Immunochemistry

Antibodies were raised in mice by intraperitoneal (IP) injection of 10–20 pmoles of protein (either upper or lower band of the approximately 40,000 dalton "doublet" CDS proteins observed after phenyl sepharose chromatography) with adjuvant—either complete Freund's adjuvant or Ribi adjuvant (Ribi Immunochem Research, Inc., Hamilton, Mont.). After four weeks and six and a half weeks, booster immunizations were made using 5–10 pmoles of either upper or lower band CDS protein either with or without incomplete Freund's adjuvant. The serum was used as immunologically active material for Western blots [Towbin et al. (1979) Proc. Natl. Acad. Sci. 76:4350–4354; U.S. Pat. No. 4,452,901 (1984)]. Antibodies specifically bound to protein immobilized on nitrocellulose were visualized by the $^{125}$I-Protein A method according to the directions of the supplier of the reagents (ICN Biomedicals, Costa Mesa, Calif.), adapted from Towbin et al. (1979, Proc. Natl. Acad. Sci. 76:4350–4354).

The antibodies elicited in mice in response to the "upper" band CDS protein cross-reacted with the two phenyl sepharose purified CDS "doublet" proteins, while the antibodies raised to the "lower" band CDS protein cross-reacted with the two phenyl sepharose purified CDS "doublet" proteins and also with the hydroxylapatite purified CDS protein which corresponds to the "lower" band of the phenyl sepharose CDS protein "doublet."

In a preferred embodiment of the invention, a peptide was chemically synthesized to have the amino acid sequence from residue 7 to residue 18 of SEQ ID NO:1. This synthetic peptide was used antigenically to immunize rabbits. A commercial company (e.g., Research Genetics, Huntsville, Ala.) carried out the immunization of rabbits. The initial immunization was with 0.75 mg of synthetic CDS peptide dissolved in 1.0 ml of tris-buffered saline and emulsified with 1.0 ml Freund's complete adjuvant. One half (1.0 ml) of the mixture was injected intradermally and the remainder was injected subcutaneously. Subsequent boosts were made by injecting subcutaneously at two and six weeks using 0.75 mg of protein in Freund's incomplete adjuvant. On Western blots antibodies to synthetic CDS peptide cross-reacts with both upper and lower band "doublet" proteins from phenyl sepharose purification and also cross-reacts with the purified CDS protein from hydroxyapatite chromatography which corresponds to the 40,000 dalton "lower" band of the "doublet."

EXAMPLE 2:

Cloning of Chrysanthemyl Diphosphate Synthase

A powerful approach for the isolation of the DNA sequence encoding a particular protein for which little information is available, is to obtain a partial amino acid sequence and use the corresponding deduced nucleotide sequence as a probe to screen a cDNA library. This approach has been used recently for the isolation and identification of a particular sequence from a tomato cDNA library [King et al. (1988) Plant Mol. Biol. 10:401]. Because the purification of chrysanthemyl diphosphate synthase yields only small quantities of protein, a microsequencing approach preceded by purification by polyacrylamide gel electrophoresis was used [Matsudaira (1990) Methods in Enzymol. 182:602–613]. The combination of gel electrophoresis followed by electroblotting onto an inert matrix yields a pure sample which can be sequenced directly. The N-terminal sequence determined for the purified CDS protein is presented in Table 2 (SEQ ID NO:1).

Because of the redundancy of the genetic code there are numerous possibilities for the nucleotide sequence in the gene coding for any given protein. This difficulty can be circumvented by using multiple probes with mixed bases at particular positions [Davisson et al. (1986) Bioorg. Chem. 14:46], and also by using a synthetic inosine at several of the degenerate positions [Ohtsuka et al. (1985) J. Biol. Chem. 260:2605–2608].

As the first step toward isolating the gene encoding chrysanthemyl diphosphate synthase, a cDNA library of *C. cinerariaefolium* flower mRNA was constructed using the method of Kimmel and Berger (1987) supra. The mRNA for the library was isolated from immature flowers of *C. cinerariaefolium* and cDNA was synthesized from poly A enriched RNA using Stratagene Zap cDNA synthesis kit. The cDNA was cloned into the Stratagene Lambda Zap vector.

From the N-terminal amino acid sequence of the CDS of *C. cinerariaefolium* a corresponding oligonucleotide probe was synthesized (Genosys Biotechnologies Inc., The Woodlands, Tex.) to code for the region of least degeneracy (residues 11–18 of SEQ ID NO:1 in Table 2). The oligonucleotide probe (Table 10) was used to initially select the candidate clone. Hybridization was carried out overnight at 49° C. in 6x SSC medium with 0.5% SDS, followed by three ten-minute Washes at 45° C. in 6x SSC medium with 0.1% SDS.

Approximately 1 million plaques from that library were screened and one clone was identified which hybridized with the oligonucleotide probe. The insert in that bacteriophage was about 1.7 kilobases, sufficient to encode a protein of 40 kilodaltons. The nucleotide sequence of the cDNA encoding the CDS protein is presented in FIG. 4. Confirmation of the identity of the cDNA as coding for chrysanthemyl diphosphate synthase is obtained from DNA sequencing and/or expression of enzymatic function. For these reasons the plasmid vector used in the cDNA cloning comprises bacteriophage promoters adjacent to the polycloning site. The *C. cinerariaefolium* cDNA inserted at the cloning site can therefore be transcribed in vitro when the linearized recombinant plasmid is incubated with the appropriate DNA-dependent RNA polymerase. A different promoter is present on either side of the polycloning site so that a transcript can be made specifically to either strand of the cDNA simply by using different RNA polymerases. RNAs generated in this manner can be used as hybridization probes or can be translated in cell-free protein synthesis systems.

In a similar manner, several synthetic oligonucleotide probes corresponding to different regions of a cDNA coding for CDS can be utilized to isolate a CDS gene from a *C. cinerariaefolium* flower genomic library. Genomic DNA from *C. cinerariaefolium* flower can be prepared by art-known methods, for example, using the procedure of Murray and Thompson (1980) Nucl. Acids Res. 8:4321–4325 and Herrman and Frischauf (1987) supra, and digested with restriction enzymes according to the instructions of the manufacturer (e.g., BRL). Hybridization of the genomic DNA fragments with labelled oligonucleotide probes, carried out according to methods available in the art, for example, King et al. (1988) Plant Mol. Biol. 10:401–412, is used to identify the gene(s) for CDS from *C. cinerariaefolium*.

Once cDNA clones which show a strong hybridization signal with the oligoprobes have been identified, they are sequenced to confirm that they are complementary to the known amino acid sequence. In addition, to show that the candidate cDNA does in fact encode chrysanthemyl diphosphate synthase, the protein encoded by the cDNA is shown to possess the enzymatic activity to convert DMAPP to chrysanthemyl diphosphate. A RNA transcript is selectively transcribed by the appropriate RNA polymerase. The transcript is then translated in a rabbit reticulocyte lysate or wheat germ extract in vitro translation system (available from BRL) and the protein product is tested for enzymatic activity.

Antibodies raised to the CDS protein are extremely useful analytically and diagnostically, for example, under conditions when the translation products do not exhibit enzyme activity. Under such conditions of inability to demonstrate CDS activity the use of antibodies to CDS to react with the product of the cloned gene is accepted as proof that the clone contains the cDNA encoding CDS. Expression of the cloned CDS gene in the recipient organism can then be optimized, [Bauw et al. (1987) Proc. Natl. Acad. Sci. USA 84:4806].

To ensure that a full-length or a sufficient length of cDNA is available for gene expression, PCR amplification of an isolated short cDNA fragment may be carried out using genomic DNA as template. This can be done using inverse PCR making primers from within the cDNA clone, [Ochman, H. et al. (1988) Genetics 120:621].

PCR is used in the original cloning of CDS cDNA to overcome the problem that a poorly expressed mRNA will be under represented in a cDNA library. A recent paper describes a PCR based method to clone a gene from genomic DNA using partial protein sequence, [Aarts, J.M.M.J.G. (1991) Plant Mol. Biol. 16:647; and Ochman et al. (1988) Genetics 120:621–623]. Sequence information obtained for two or more CNBr fragments of one protein is used to amplify a segment of the gene by making oligonucleotide primers to a region of each fragment in both directions and testing pairwise combinations of the primers for amplification. One combination amplifies the region between the two fragments. This amplification product can then be used as a probe to screen a cDNA library (longer probes give a stronger signal and therefore more positive identification). Alternatively, the amplification product can be made oriented out from the product to be used in inverse PCR reactions.

EXAMPLE 3

Screening Yeast for Metabolism/Excretion of Chrysanthemyl Alcohol

The goal of this project is to produce chrysanthemyl alcohol to serve as substrate for the chemical synthesis of pyrethrin. After identifying the clone which encodes chrysanthemyl diphosphate synthase, the most expedient way to produce chrysanthemyl alcohol is to transform the clones into yeast and allow the yeast cell to convert chrysanthemyl diphosphate to the corresponding alcohol. Industrial yeasts are now amenable to genetic transformation using dominant selectable markers. A collection of yeast strains is available, for example, from ATCC, Rockville, Md.; from Dr. Linda Bisson at University of California, Davis; from ZeaGen, Fort Collins, Colo.; etc. There are several properties for which the yeast are screened. First, the yeast is selected for very low or no catabolic activity of chrysanthemyl alcohol. Secondly, yeast is selected for a strong ability to excrete the alcohol and tolerate high levels of the alcohol in the growth medium. Additionally, yeast is selected for the ability to cleave chrysanthemyl diphosphate to the alcohol. Yeast contain both an acid and an alkaline phosphatase which are associated with the vacuole. The alkaline phosphatase has been shown to be a vacuolar membrane protein. The chrysanthemyl diphosphate is transported into the vacuole in order for phosphatase to cleave it, and this may occur as a result of the overproduction of this compound in the transformed yeast cell. It is possible that when grown in limiting phosphate, the yeast cell cleaves the phosphate off the chrysanthemyl diphosphate and excretes the chrysanthemol in an effort to halt the accumulation of chrysanthemyl diphosphate and also to conserve phosphate. Alternatively, it may be necessary to isolate the chrysanthemyl diphosphate and subsequently convert it to the corresponding alcohol enzymatically with alkaline or acid phosphatases, or chemically through basic hydrolysis with either sodium bicarbonate or dilute sodium hydroxide.

Yeast transformation techniques have been developed over the past decade and have been described in detail in the literature. Successful expression of various foreign proteins including plant proteins has been reported, [Goodey, A. R. et al. (1987) Yeast Biotechnology (Berry, et al., eds.) Allen Unwin, pp. 401–429; Tague, B. (1987) J. Cell. Biol. 105:1971; Rothstein, S. J. et al. (1984) Nature 308:662; Parent, S. et al. (1985) Yeast 1:83]. Numerous host and vectors are publicly available. The selection of appropriate strains and conditions of growth which allow the production and recovery of chrysanthemyl alcohol, for example, by steam distillation, is determined using procedures routine in the art.

EXAMPLE 4

Isolation of Chrysanthemol from Yeast Broth

The feasibility of utilizing steam distillation as a method for isolating chrysanthemyl alcohol from fermentation broth was determined. A 0.1% mixture of chrysanthemyl alcohol in growth media is known to be lethal to the yeast strain, UCD522. Assuming this value to be the maximum amount of chrysanthemyl alcohol that will be present in the broth, two mixtures were prepared. One contained 1 ml of chrysanthemyl alcohol in 1 l of water and the second contained 1 ml of chrysanthemyl alcohol in 1 l of yeast broth that had been clarified by centrifugation. The mixtures were then distilled at atmospheric pressure and 50 ml fractions were collected. Each fraction was then extracted with 3×20 ml of pentane. The pentane fractions were diluted to a known volume in volumetric flasks and analyzed by gas chromatography. A standard was prepared using 1 ml of chrysanthemyl alcohol as a 100% reference. The percentage listed in Table 12 below of the individual fractions are relative to this standard.

TABLE 12

| Steam Distillation of Chrysanthemyl Alcohol From Water and Yeast Broth | | |
|---|---|---|
| | Fraction # | Chrysanthemol recovered |
| 0.1% Chrysanthemol in water | 1 | 76% |
| | 2 | 16% |
| | 3 | 0.5% |
| 0.1% Chrysanthemol in broth | 1 | 106% |
| | 2 | 7% |
| | 3 | 3% |

The stability of the metabolite in the yeast broth and the percent recovery as reported in Table 12 indicates the feasibility of isolating chrysanthemyl alcohol from fermentation broth, for example, by using a steam distillation procedure.

EXAMPLE 5

Chemical Transformation of Chrysanthemyl Alcohol into Pyrethrin (a) Synthesis of the Rethrolone Moiety Hydroxycyclopentenones (rethrolones) are the alcoholic components of the pyrethrin esters found in *Chrysanthemum cinerariaefolium*. Intense interest has been generated in the synthesis of these keto-alcohols and a large number of methods are known for the preparation of various cyclopentenones. Some references relevant to the synthesis of rethrolones are, among others, Romanet and Schlessinger (1974) J. Am. Chem. Soc. 96(11):3701–3702; Curran (1983) Tetrahedron Lett. 24(33):3443–3446; Shono et al. (1976) Chemistry Letters, pp. 1249–1552; Takahashi et al. (1981) Chemistry Letters, pp. 1189–1192; and Hirohara et al. (1985) Stud. Org. Chem. 22:119-34.

(b) Oxidation of Chrysanthemol to Chrysanthemic Acid

The immediate product of the enzymatic condensation of dimethylallyl pyrophosphate is chrysanthemyl diphosphate. Hydrolysis of the diphosphate to the free alcohol, if needed, is accomplished through basic hydrolysis with either sodium bicarbonate or dilute sodium hydroxide. Oxidation of chrysanthemyl alcohol to chrysanthemic acid is performed using one of the various oxidizing agents used routinely for this reaction. For example, Singh et al. (1979) Tetrahedron 35(14):1789 have reported good yields for this oxidation using pyridinium chromate on silica and Dalton et al. (1980) U.S. Pat. No. 4,225,694 reported a 77% yield when using alkali metal perhalates or hypohalates in the presence of ruthenium dioxide. Other workers have reported good results with Jones reagent [Bhat et al. (1981) Indian J. Chem. Sect. B, 20(B) (3):204], Sarett reagent [Sasaki et al. (1973) J. Org. Chem. 38(24):4095], and chromium trioxide [Gopichand et al. (1975) Indian J. Chem. 13:433], in addition to various other methods, for example, Dalton et al. (1975) U.S. patent application Ser. No. 616,260; Dalton et al. (1980) U.S. Pat. No. 4,225,694.

(c) Esterification of Chrysanthemic Acid and Rethrolones to produce Pyrethrin I

Because of the large number of varied syntheses for preparing both chrysanthemic acid and rethrolones, there has been a considerable amount of work done on merging these two components. The most effective esterification methods utilize a catalytic amount of toluenesulfonic acid and gentle heat, triethylamine, or dicyclohexyldiimide and N-dimethylamino pyridine, (Martel et al., U.S. Pat. No. 4,489,093; Agrimiro-Marcos et al., German Patent 3,445,504; Kovacs et al., German Patent 3,023,718; Schwarze et al., European Patent Application 31,023; Martel et al., U.S. Pat. No. 3,997,586; Mastui et al., European Patent Application 50,454; Ackermann et al., French Patent 2,478,085). In another method by Crombie et al. (1985) J. Chem. Soc. Perkin Trans. I, p. 1393, pyrethrins I were isolated as crystalline semicarbazones (semicarbazide hydrochloride, sodium acetate, pyridine) to give high yields of product. Alternatively, the acid chloride of chrysanthemic acid can be prepared by treating with oxalyl chloride and then esterified with the rethrolone by stirring in pyridine. The methods determined to be the most efficient procedure for high yield preparation is the one adopted for the esterification reactions.

(d) Allylic Oxidation to produce Pyrethrin II

There are a large number of methods available in the art to effect the conversion of chrysanthemol and/or chrysanthemic acid to pyrethric acid with subsequent formation of pyrethrin I and pyrethrin II. The scheme presented in FIG. 3 outlines one such procedure wherein chrysanthemol is oxidized to chrysanthemic acid or pyrethric acid, both of which are subsequently esterified with rethrolone moieties to produce pyrethrin I or II.

In an alternative embodiment, chrysanthemic acid is converted to pyrethric acid, by cleavage of the olefinic moiety (by ozonolysis, etc.) to form the corresponding aldehyde, followed by the Wittig reaction in the presence of the alkyltriphenylphosphonium reagent (see Science (1980) 207:42–44). Pyrethric acid is then esterified with rethrolone to produce pyrethrin II using the general synthetic procedure outlined herein for the synthesis of pyrethrin I from chrysanthemic acid, with the additional precaution of blocking the methyl ester side chain of pyrethric acid.

EXAMPLE 6

Chemical Synthesis of Dimethylallyl Pyrophosphate (DMAPP)

Figure 6:
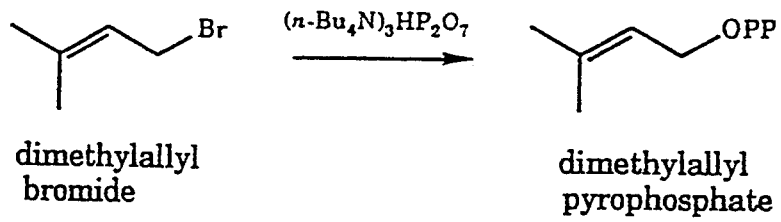
FIG. 6 presents chemical structures in the synthesis of dimethylallyl pyrophosphate (DMAPP).

Dimethylallyl pyrophosphate (DMAPP) was synthesized by the method of Poulter and coworkers [Dixit et al. (1981) J. Org. Chem. 46:1967; Davisson et al. (1986) Bioorg. Chem. 14:46; Davisson et al. (1986) J. Org. Chem. 51:4768; and Davisson et al. (1985) Methods Enzymol. 110:130]. Commercially available dimethylallyl bromide (3-methyl-2-buten-1-yl bromide) was treated with freshly prepared tris (tetra-n-butylammonium) hydrogen pyrophosphate [Dixit et al. (1981) J. Org. Chem. 46:1967–1970 and Davisson et al. (1986) J. Org. Chem. 51:4768] and the resulting material was converted to the ammonium salt of DMAPP (see FIG. 6.)

[1-$^3$H]DMAPP is prepared following the established literature methods of Davisson et al. (1986) Bioorganic Chem. 14:46.

EXAMPLE 7

Biosynthesis of Pyrethroids (+)-trans-Pyrethroids are produced by the esterification of (+)-trans-chrysanthemic acid with a desired cyclic alcohol. The specific isomer, (+)-trans-chrysanthemic acid, is produced by the enzymatic conversion of DMAPP to (+)-trans-chrysanthemyl diphosphate, followed by the conversion of chrysanthemyl diphosphate to chrysanthemyl alcohol and oxidized of the alcohol to the corresponding acid. The enzymatic synthesis of the natural isomer of chrysanthemyl diphosphate is accomplished utilizing the purified CDS of the invention (Example 1) or, preferably, utilizing a DNA fragment encoding CDS to express CDS activity for production of the natural [(+)-trans-] isomer of chrysanthemyl diphosphate (see Example 2). The conversion of (+)-trans-chrysanthemyl diphosphate to the corresponding alcohol is carried out as described in Example 3. (+)-trans-Chrysanthemyl alcohol is isolated according to the procedure of Example 4 and is oxidized to chrysanthemic acid as described in Example 5(b).

(+)-trans-Chrysanthemic acid is esterified with a desired cyclic alcohol, e.g., 3-phenoxybenzyl alcohol, 3-phenoxybenzaldehyde, 3-phenoxybenzylcyanohydrin, 5-benzyl-3-furylmethyl alcohol, derivatives thereof, etc. Methods for the synthesis of active pyrethroids utilizing chrysanthemic acid and a desired alcohol are publicly available, for example, see Carter, S. W. (1989) "A Review of the Use of Synthetic Pyrethroids in Public Health and Vector Pest Control," Pesticide Science 27:361–374; Cromby, L. (ed.) Recent Advances in the Chemistry of Insect Control II. Royal Society of Chemistry Special Publication No. 79; Elliott, M. (1989) "The Pyrethroids—Early Discovery, Recent Advances and the Future," Pesticide Science 27:337–351; Hill, I. R. (1989) "Aquatic Organisms and Pyrethroids," Pesticide Science 27:429–457; Leahey, J. P. (1985) The Pyrethroid Insecticides, Published by Taylor & Francis; Naumann, K., Chemistry of Plant, Protection, Vols. 4 & 5—"Synthetic Pyrethroids Parts I and II, published by Springer Verlag; Saini, R. K. et al. (1989) "Development of Insecticide Resistance and Cross-Resistance in Fenvalerate- and Cypermethrin-Selected Strains of Earias vinella," Pesticide Science 25:289–295; and Watkinson, I. A. (1989) "Pyrethroids and the Economics of Pest Management," Pesticide Science 27:465. Derivatives of pyrethroids can be formulated to include, for example, non-ester pyrethroids, silicon-substituted pyrethroids, halogenated pyrethrins, and the like.

A (+)-trans-pyrethroid produced by this procedure is the desired active optical isomer and is present as a single isomeric species. This invention obviates the need currently present in the art to separate racemic mixtures in order to obtain a single desired isomeric species.

EXAMPLE 8

Metabolite Biosynthesis

A (+)-trans-isomer obtained by the CDS activity of the Applicants' invention is utilized for the synthesis of several classes of metabolites, including sterols, carotenoids, dolichols and ubiquinones. The enzymatic synthesis of the natural isomer of chrysanthemyl diphosphate is accomplished utilizing the purified CDS of the invention (Example 1), or preferably, utilizing a DNA fragment encoding CDS (Example 2) to express CDS activity for the subsequent production of the natural (+)-trans-isomer of a desired substrate. Methods useful in the synthesis of a desired isoprenoid compound, e.g., a sterol, carotenoid, dolichol, ubiquinone, etc., are found in Croteau (1981) in *Biosynthesis of Isoprenoid Compounds*, Porter, J. W. and Spurgeon, S., (eds.), Vol 1, Wiley, New York, pp. 255–292; Cane, D. E. (1981) in *Biosynthesis of Isoprenoid Compounds*, Porter, J. W. and Spurgeon, S. L., (eds.), Vol 1, Wiley, New York, pp. 283–374; and Poulter, C. D. and Rilling, H. C. (1981) in *Biosynthesis of Isoprenoid Compounds*, Porter, J. W. and Spurgeon, S. L., (eds.), Vol 1, Wiley, N.Y., pp. 414–441.

We claim:

1. A cloned DNA encoding a chrysanthemyl diphosphate synthase capable of catalyzing the conversion of dimethylallyl pyrophosphate to chrysanthemyl diphosphate, said cloned DNA hybridizing under stringent conditions to a nucleotide sequence comprising SEQ ID NO: 9 or SEQ ID NO: 10 and wherein said cloned DNA is extracted and purified from a chrysanthemyl diphosphate synthase-containing or pyrethrin-producing species of the family Compositae.

2. The cloned DNA of claim 1 wherein said species is selected from the group consisting of Chrysanthemum, Artemisia, Santolina, Anacyclus, or Tagetes of the family Compositae.

3. The cloned DNA of claim 2 wherein said cloned DNA is extracted and purified from *Chrysanthemum cinerariaefolium*.

4. The cloned DNA of claim 3 wherein said chrysanthemyl diphosphate synthase comprises an N-terminal amino acid sequence comprising SEQ ID NO:1.

5. The cloned DNA of claim 4 wherein said chrysanthemyl diphosphate synthase further comprises an amino acid sequence selected from the group of amino acid sequences consisting of SEQ ID NO:3, SEQ ID NO:4, SEQ ID NO:5, SEQ ID NO:6, SEQ ID NO:7 AND SEQ ID NO:8.

6. The cloned DNA of claim 1 wherein said chrysanthemyl diphosphate synthase is immunologically cross-reactive with an antibody to an amino acid sequence consisting of residue 7 to residue 18 of SEQ ID NO:1.

7. The cloned DNA of claim 1 wherein said chrysanthemyl diphosphate synthase is immunologically cross-reactive with an antibody to a purified chrysanthemyl diphosphate synthase encoded by a nucleotide sequence hybridizing under stringent conditions to a nucleotide sequence comprising SEQ ID NO:9 or SEQ ID NO:10.

8. The cloned DNA of claim 1 wherein said cloned DNA comprises a nucleotide sequence that is SEQ ID NO:10.

9. A cloned DNA encoding a chrysanthemyl diphosphate synthase capable of catalyzing the conversion of dimethylallyl pyrophosphate to chrysanthemyl diphosphate, said cloned DNA comprising the nucleotide sequence of SEQ ID NO: 10 or a nucleotide sequence encoding the chrysanthemyl diphosphate synthase amino acid sequence encoded by the nucleotide sequence of SEQ ID NO: 10.

10. A DNA recombinant vector comprising a DNA of claim 1.

11. A DNA recombinant vector comprising a DNA of claim 2.

12. A DNA recombinant vector comprising a DNA of claim 3.

13. A DNA recombinant vector comprising a DNA of claim 6.

14. A DNA recombinant vector comprising a DNA of claim 8.

15. A procaryotic or eucaryotic host cell transformed with a DNA of claim 1 so that chrysanthemyl diphosphate synthase activity is expressed, producing enzymatically a (+)-trans-isomer.

16. A procaryotic or eucaryotic host cell transformed with a DNA of claim 2 so that chrysanthemyl diphosphate synthase activity is expressed, producing enzymatically a (+)-trans-isomer.

17. A procaryotic or eucaryotic host cell transformed with a DNA of claim 3 so that chrysanthemyl diphosphate synthase activity is expressed, producing enzymatically a (+)-trans-isomer.

18. A procaryotic or eucaryotic host cell transformed with a DNA of claim 6 so that chrysanthemyl diphosphate synthase activity is expressed, producing enzymatically a (+)-trans-isomer.

19. A procaryotic or eucaryotic host cell transformed with a DNA of claim 8 so that chrysanthemyl diphosphate synthase activity is expressed, producing enzymatically a (+)-trans-isomer.

20. A procaryotic or eucaryotic host cell transformed with a DNA recombinant vector of claim 10 so that chrysanthemyl diphosphate synthase activity is expressed, producing enzymatically a (+)-trans-isomer.

21. A procaryotic or eucaryotic host cell transformed with a DNA recombinant vector of claim 11 so that chrysanthemyl diphosphate synthase activity is expressed, producing enzymatically a (+)-trans-isomer.

22. A procaryotic or eucaryotic host cell transformed with a DNA recombinant vector of claim 12 so that chrysanthemyl diphosphate synthase activity is expressed, producing enzymatically a (+)-trans-isomer.

23. A procaryotic or eucaryotic host cell transformed with a DNA recombinant vector of claim 13 so that chrysanthemyl diphosphate synthase activity is expressed, producing enzymatically a (+)-trans-isomer.

24. A procaryotic or eucaryotic host cell transformed with a DNA recombinant vector of claim 14 so that chrysanthemyl diphosphate synthase activity is expressed.

25. The host cell of claim 15 wherein said host cell is a strain of yeast.

26. The host cell of claim 25 wherein said host cell is *Saccharomyces cerevisiae*.

27. The host cell of claim 15 wherein said host cell is a bacterium.

28. The host cell of claim 27 wherein said host cell is *Escherichia coli*.

29. A genetically-engineered DNA molecule comprising a chrysanthemyl diphosphate synthase gene of claim 1 under control of a heterologous constitutive promoter so that chrysanthemyl diphosphate synthase activity is expressed, producing enzymatically a (+)-trans-isomer.

30. A genetically-engineered DNA molecule of claim 29 wherein said chrysanthemyl diphosphate synthase is encoded by a gene hybridizing under stringent conditions to a nucleotide sequence comprising SEQ ID NO:9.

31. The genetically-engineered DNA molecule of claim 29 wherein said chrysanthemyl diphosphate synthase gene comprises the nucleotide sequence of SEQ ID NO:10.

32. The genetically-engineered DNA molecule of claim 29 wherein said chrysanthemyl diphosphate synthase gene encodes a protein comprising an N-terminal amino acid sequence comprising SEQ ID NO:1.

33. The genetically engineered DNA molecule of claim 29 wherein said chrysanthemyl diphosphate synthase gene encodes a chrysanthemyl diphosphate synthase that is immunologically cross-reactive with an antibody to an amino acid sequence consisting of residue 7 to residue 18 of SEQ ID NO:1.

34. The genetically-engineered plant chrysanthemyl diphosphate synthase gene of claim 29 wherein said chrysanthemyl diphosphate synthase gene encodes a chrysanthemyl diphosphate synthase that is immunologically cross-reactive with an antibody to a purified chrysanthemyl diphosphate synthase encoded by a nucleotide sequence hybridizing under stringent conditions to a nucleotide sequence comprising SEQ ID NO:9 or SEQ ID NO:10.

35. The genetically-engineered plant chrysanthemyl diphosphate synthase gene of claim 29 wherein said constitutive promoter is selected from a group consisting of a bacterial promoter and a viral promoter.

* * * * *